(12) United States Patent
Berggren et al.

(10) Patent No.: US 8,137,524 B2
(45) Date of Patent: Mar. 20, 2012

(54) ELECTRICALLY CONTROLLED ION TRANSPORT DEVICE

(75) Inventors: Magnus Berggren, Vreta Kloster (SE); Peter Kjäll, Lidingö (SE); David Nilsson, Vikingstad (SE); Nathaniel D. Robinson, Kolmården (SE); Agneta Richter Dahlfors, Saltsjö-Boo (SE); Joakim Isaksson, Norrköping (SE)

(73) Assignee: Oboe IPR AB, Norrkoping (SE)

( * ) Notice: Subject to any disclaimer, the term of this patent is extended or adjusted under 35 U.S.C. 154(b) by 1308 days.

(21) Appl. No.: 11/806,743

(22) Filed: Jun. 4, 2007

(65) Prior Publication Data

US 2008/0023339 A1    Jan. 31, 2008

(30) Foreign Application Priority Data

Jun. 2, 2006   (EP) .................................. 06114939

(51) Int. Cl.
*B01D 61/44*   (2006.01)
(52) U.S. Cl. ......... 204/630; 204/627; 204/606; 204/605
(58) Field of Classification Search .................. 204/627, 204/630, 606, 605
See application file for complete search history.

(56) References Cited

U.S. PATENT DOCUMENTS

| | | | |
|---|---|---|---|
| 5,405,509 A * | 4/1995 | Lomasney et al. ............ | 205/688 |
| 5,779,325 A | 7/1998 | Diesel | |
| 6,770,180 B1 | 8/2004 | Diehl | |
| 6,780,584 B1 | 8/2004 | Edman et al. | |

FOREIGN PATENT DOCUMENTS

| | | |
|---|---|---|
| EP | 0 771 671 | 5/1997 |
| WO | WO 96/01681 | 1/1996 |
| WO | WO 03/025953 | 3/2003 |

(Continued)

OTHER PUBLICATIONS

Ghosh et al., "Networks of Electron-Conducting Polymer in Matrices of Ion Conducting Polymers," *Electrochemical & Solid State Letters*, 3(5) pp. 213-215 (2000).

(Continued)

*Primary Examiner* — Arun S Phasge
(74) *Attorney, Agent, or Firm* — Harness, Dickey & Pierce, P.L.C.

(57) ABSTRACT

A device is disclosed for electrically controlled transport of ions between a source and a target electrolyte, including a source electrode and a target electrode. The electrodes are each capable of conducting ions, and the source electrode is arranged to receive ions from the source electrolyte and the target electrode is arranged to release ions to the target electrolyte. The device further includes an ion-conductive channel, arranged to receive ions from the source electrode and to release ions to the target electrode. Moreover, the ion-conductive channel is arranged to provide an ionic connection between the source and the target electrodes. The electrodes and the ion-conductive channel are formed of solid or semi-solid materials which are directly or indirectly attached to a support. In at least one embodiment, the device also includes a device for limiting an electronic current between the source and the target electrodes, such that at least after a voltage is applied across the channel a potential difference between the source and target electrodes is maintained, which potential difference effects ion transport from said source to the target electrode. An apparatus for transporting ions to or from a cell, use of the device for transporting ions to or from a cell, and methods of operating the device are also disclosed.

49 Claims, 13 Drawing Sheets

FOREIGN PATENT DOCUMENTS

WO  WO 2005/053836  6/2005

OTHER PUBLICATIONS

Nilsson et al., "Electrochemical Logic Circuits," *Advanced Materials*, vol. 17, No. 3, pp. 353-358 (Feb. 10, 2005).

Search Report dated Dec. 1, 2006 for corresponding European Application No. 06114939.9.

Gustafsson et al., "In situ spectroscopic investigations of electrochromism and ion transport in a poly(3,4-ethylenedioxythiophene) electrode in a solid state electrochemical cell," *Solid State Ionics*, vol. 69, pp. 145-152 (1994).

Kossmehl et al., "Application of Electrically Conductive Polythiophenes," *Handbook of Oligo- and Polythiophenes*, D. Fichou, Ed., Wiley-VCH, Weinheim, Germany, pp. 491-524 (1999).

Schottland et al., "Poly(3,4-alkylenedioxypyrrole)s: Highly stable Electronically Conducting and Electrochromic Polymers," *Macromolecules*, vol. 33, pp. 7051-7061 (2000).

Onoda et al., Properties of Electrochemically Cation-Doped Poly(isothianaphthene), *J. Electrochem. Soc.*, vol. 141, No. 2, pp. 338-341 (Feb. 1994).

P. Chandrasekhar, "Conducting Polymers, Fundamentals and Applications, A Practical Approach," Kluwer Academic Publishers, Boston, Ch. 20, pp. 543-562 (1999).

A.J. Epstein, "Novel Concepts in Electronic Polymers: Polyaniline and its Derivatives," *Makromol. Chem.*, Macromol Symp, vol. 51, pp. 217-237 (1991).

"Modern Coating and Drying Technology," Edward D. Cohan & Edgar B. Gutoff, Eds., VCH Publishing Inc., New York, pp. 1-21 (1992).

\* cited by examiner

ELECTRICALLY CONTROLLED ION TRANSPORT DEVICE

PRIORITY STATEMENT

The present application hereby claims priority under 35 U.S.C. §119 on European patent application number EP 06114939.9 filed Jun. 2, 2006, the entire contents of which is hereby incorporated herein by reference.

FIELD OF THE INVENTION

The present invention relates to a device for electrically controlled transport of ions between a source and a target electrolyte, and to an apparatus for transporting ions to or from a cell. The present invention further relates to the use of such a device for transporting ions to or from a cell, and to methods of operating such a device.

BACKGROUND

Ion signalling in eukaryotic cells is essential for numerous physiological processes, including regulation of exocytosis, contraction, gene transcription and fertilization, as well as maintenance of cell membrane potential. Ion signalling is equally important in prokaryotic cells, e.g. in osmoregulation. Ion signalling in cells may be affected by alteration of extracellular and intracellular concentration of ions. Such alterations result in intracellular concentration changes in the forms of i) rapid increase followed by a rapid decrease (termed spikes), ii) a sustained, elevated concentration, or iii) repetitive spikes that produce an oscillation of characteristic frequency and amplitude. Due to technical limitations of available methods to decipher these complex signalling pathways, very little is known about the molecular and physiological effects on cells. A limitation of certain concern is the inability of available methods to provide controlled ion fluxes to cells to be studied.

Presently, transport of ions from, to or between electrolytes, such as from a stock solution to a cell culture medium, is performed by manual or automated use of e.g. pipettes, pumps or membranes. Such techniques result in unspecific delivery of ions to a cell culture medium as such only, whereas further diffusion to cells cultured in the medium is uncontrollable and unpredictable. Furthermore, said techniques require the use of expensive equipment. Examples of present methods for transport of ions are given below.

U.S. Pat. No. 6,780,584 discloses a device for the modulation of a reaction comprising: a first buffer reservoir containing a first buffer and a first charged entity, wherein the first buffer has an initial conductance less than 1000 μS/cm; a second buffer reservoir separated from the first buffer reservoir containing a second buffer comprising a second charged entity, wherein the second charged entity has a charge opposite that of the first charged entity, the second charged entity modulates the specific reaction between the specific binding entity and the first charged entity; a conductive semi permeable matrix contained in a non-conductive support material, the conductive semi permeable matrix disposed between and fluidically connecting the first buffer reservoir and the second buffer reservoir; a first electrode linked to a power source and located in the first buffer reservoir and contacting the first buffer; and a second electrode linked to the power source and located in the second buffer reservoir and contacting the second buffer; and a specific binding entity which reacts specifically with the first charged entity and which is physically fixed on, in, or adjacent to the semi permeable matrix.

U.S. Pat. No. 5,776,325 discloses a method of inducing mono-directional transport of ions between electrolyte solutions comprising separating the electrolyte solutions with a conducting polymer membrane and creating a potential gradient across said membrane wherein the potential gradient is created by using the conducting polymer membrane as a shared working electrode.

SUMMARY OF THE INVENTION

An object of the present invention is to provide a device which is capable of transporting ions from a source electrolyte to a target electrolyte, in which device the ion transport can be electrically controlled.

Another object of the invention is to provide an ion transport device allowing ions from a source electrolyte to be delivered to a target electrolyte in a time and space resolved manner.

Yet another object of the invention is to provide an ion transport device allowing design of logic circuits or matrix addressing for delivery of ions.

A further object of the present invention is to provide a device for electrically controlled ion transport, which device can be deposited on a wide range of different rigid or flexible substrates by conventional printing methods.

A further object of the present invention is to provide an apparatus that may be used in cell communication research. In such apparatus, controlled ion fluxes to, or from, cells to be studied are achieved by means of the inventive device in its ability to transport ions in a time and space resolved manner. Ion fluxes of even higher specificity may be provided by means of e.g. matrix addressing of inventive devices for the delivery of ions to, or removal of ions from, single cells or in the sub-cellular scale. Accordingly, an additional object of the present invention is to provide use of the inventive device in cell communication research.

The above-mentioned objects, as well as further objects of the invention, which should be apparent to a person skilled in the art after having studied the description below, are achieved by the different aspects of the present invention as described herein.

According to one aspect thereof, the present invention provides a device for electrically controlled transport of ions between a source and a target electrolyte, comprising a source electrode and a target electrode. The electrodes are each capable of conducting ions, and the source electrode is arranged to receive ions from the source electrolyte and the target electrode is arranged to release ions to the target electrolyte. The device further comprises an ion-conductive channel, arranged to receive ions from the source electrode and to release ions to the target electrode. Moreover, the ion-conductive channel is arranged to provide an ionic connection between the source and the target electrodes. The electrodes and the ion-conductive channel are formed of solid or semi-solid materials which are directly or indirectly attached to a support. The device also comprises means for limiting an electronic current between said source and said target electrodes, such that at least after a voltage is applied across said channel a potential difference between said source and target electrodes is maintained, which potential difference effects ion transport from said source to said target electrode. Preferably, the device further comprises means for retaining one of said source and target electrolytes on the device, arranged such that the electrolyte is in contact with the desired electrodes.

Thus, the invention involves limiting an electronic current, i.e. a current or flow of electrons, in a material, while maintaining the ion conductivity of the material. A limitation of the electronic current in the material can e.g. be achieved by limiting the electron conductivity. This limitation makes it possible to maintain a potential difference over the material when a voltage is applied across it. The potential difference can then be used as a driving force for ion transport from one portion of the material to another.

A second aspect of the present invention relates to an apparatus for transporting ions to or from, respectively, a cell, comprising a device as defined herein and a related cell contact site arranged to provide ionic contact between the cell and the target or source electrolyte, respectively. A third aspect of the present invention relates to the use of a device as defined herein for transporting ions to or from, respectively, a cell. Preferably, use of an ion transport device for transporting ions from a source electrolyte to a target electrolyte, wherein said device comprises:

a source electrode and a target electrode, each capable of conducting ions and electrons, wherein said source electrode is arranged to receive ions from said source electrolyte and said target electrode is arranged to release ions to said target electrolyte, and an ion-conductive channel, arranged to receive ions from said source electrode, to release ions to said target electrode and to provide an ionic connection between said source and said target electrodes, wherein said electrodes and said ion-conductive channel are formed of solid or semi-solid materials which are directly or indirectly attached to a support, and further comprising means for limiting an electronic current between said source and said target electrodes, such that at least after a voltage is applied across said channel a potential difference between said source and target electrodes is maintained, which effects ion transport from said source to said target electrode. Preferably, said source electrolyte or said target electrolyte comprises a cell. When a cell is present in said source electrolyte or said target electrolyte, said target or source electrolyte, respectively, may preferably comprise a cell culture medium. In an embodiment, said cell is present on said target or source electrode.

Thus, by the present invention is provided an apparatus or the use of a device by which ions are transported to prokaryotic or eukaryotic cells, including tissue, cultivated or otherwise present on the target electrode or in the target electrolyte. By means of direct or indirect action, transported ions may affect said cells and induce biological processes therein. Accordingly, the present invention is useful in cell communication research, wherein said apparatus or device can be utilized for delivering ions to cells in order to allow evaluation of the response of said cells.

The device may also be used to transport ions in the opposite direction, i.e. from a cell, in order to analyze ionic species that are excreted from a cell under certain conditions. In other words, the inventive device may be used as a means for delivery of ions to cells, as well as a part of an arrangement for analyzing cellular response.

According to a fourth aspect thereof, the present invention relates to methods of operating devices as defined herein to effect electrically controlled transport of ions between a source and a target electrolyte, as defined in the appended claims.

Ions:

The term "ion" as used herein encompasses not only positively or negatively charged monovalent or multivalent ionic species of atomic elements, but also other molecular species carrying a net positive or negative charge. Hence, in an embodiment of the invention it is intended to transport charged biologically active molecules or macromolecules such as charged amino acids, proteins, vitamins, peptides or hormones. In one embodiment of the invention, the ions that may be transported are cations, for example metal ions, such as potassium or calcium ions. In another embodiment of the invention the ions that may be transported are anions.

Ionic Contact:

A first and a second material are in ionic contact when a substantial amount of ions comprised in the first material can move from the first material to the second material, possibly via a third material. The ionic movement may be caused by diffusion or by an applied electric field.

A material which provides an ionic connection between a first and a second material, is a material which is ionically conductive and in ionic contact with both said first and said second material.

Directly or Indirectly Attached:

Two parts which are directly attached to each other are in direct physical contact with each other. With respect to this invention, when a first part is directly attached to a second part, which second part is directly attached to a third part, said first and third parts are referred to as being indirectly attached to each other. Similarly, when said third part is directly attached to a fourth part, said first and fourth parts are referred to as being indirectly attached to each other.

Semi-Solid Material:

The term semi-solid material refers to a material, which at the temperatures at which it is used has a rigidity and viscosity intermediate between a solid and a liquid. Thus, the material is sufficiently rigid such that it does not flow or leak. Further, particles/flakes in the bulk thereof are substantially immobilized by the high viscosity/rigidity of the material.

In a preferred case, a semi-solid material has the proper rheological properties to allow for the ready application of it on a support as an integral sheet or in a pattern, for example by conventional printing methods. After deposition, the formulation of the material should preferably solidify upon evaporation of solvent or because of a chemical cross-linking reaction, brought about by additional chemical reagents or by physical effect, such as irradiation by ultraviolet, infrared or microwave radiation, cooling etc.

The semi-solid or solidified material preferably comprises an aqueous or organic solvent-containing gel, such as gelatin or a polymeric gel.

Electrochemically Active Material:

With respect to this invention the term electrochemically active material refers to a material which is capable of being oxidized or reduced when it is in contact with an electrolyte and a voltage is maintained across it. Examples of such electrochemically active materials include electrically conductive polymers, as will be described below, and certain metal oxides, such as indium tin oxide (ITO) and tungsten oxide ($WO_3$). Changing of the oxidation state of an electrochemically active material may result in a change in optical and conductivity properties of the material.

Electrolyte:

The electrolyte for use with the device or method of the present invention should preferably be based on a solvent which permits ionic conduction in the electrolyte, i.e. which allows for the dissociation of ionic substances such as salts, acids, bases etc. The solvent and/or the ionic substance may contribute nucleophiles. Possible electrolytes for use in combination with the inventive device are solutions of salts, acids, bases, or other ion-releasing agents in solvents that support the dissociation of ionic species, thus allowing ionic conductivity. In applications where it is required, the electrolytes may comprise buffer solutions, such as buffer solutions suitable for use with living organisms or biomolecules, such as proteins. Examples of such buffers include $NaHPO_4$ and sodium acetate. As other non-limiting examples of possible electrolytes, mention can be made of: aqueous solutions of potassium acetate, calcium acetate, NaCl, $Na_2SO_4$, $H_3PO_4$, $H_2SO_4$, KCl, $RbNO_3$, $NH_4OH$, CsOH, NaOH, KOH, $H_2O_2$; organic solvents such as acetonitrile, pyridine, DMSO, DMF, dichloromethane, etc., in combination with suitable salts, such as lithiumperchlorate and tertiary ammonium salts, e.g. tetra-butyl ammonium chloride; inorganic solvents such as hypercritical $CO_2$, liquid $SO_2$, liquid $NH_3$, etc., in combination with salts that dissociate in these solvents; solvents displaying auto-dissociation, which results in the formation of ionic species, such as water, formic acid and acetic acid. The term electrolyte also encompasses solutions comprising charged biologically active molecules or macromolecules such as charged amino acids, proteins, vitamins, peptides or hormones. An electrolyte may also comprise cell culturing media or ingredients thereof, such as proteins, amino acids, vitamins and growth factors.

The electrolyte may also be in a semi-solid or solidified form, preferably comprising an aqueous or organic solvent-containing gel as described above. However, solid polymeric electrolytes are also contemplated and fall within the scope of the present invention. Furthermore, the term electrolytes also encompasses liquid electrolyte solutions soaked into, or in any other way hosted by, an appropriate matrix material, such as a paper, a fabric or a porous polymer.

Electrodes:

The source and target electrodes of the inventive device each comprises a material or a combination of materials which is capable of conducting both ions and electrons. The molecular structure of an electrode should allow for ions of at least a low molecular weight to enter the electrode via an electrolyte in ionic contact with the material, and for these ions to move within the material with some degree of freedom.

Ion conductivity and electron conductivity may be provided by the same material. Examples of materials which are able to conduct both ions and electrons are some electrically conductive polymers as will be described in greater detail below.

It is also possible to use a combination of two or more materials where at least one of the materials is electronically conductive and at least one of the materials is capable of conducting ions. Examples of such combinations, which may be used in a device according to the present invention, include an electronically conductive material, such as indium tin oxide, and an ion-conductive hydrogel.

The electrodes may also comprise further organic or inorganic materials, which are capable of conducting ions but not capable of conducting electrons, which materials are included in order to facilitate ion transport into and within the electrodes. Examples of such materials are polymer materials, such as hydrogels and polyelectrolytes. Such additional electrode materials may be either dispersed in, or be arranged as a separate layer in contact with, an electronically conductive electrode material.

The electrodes of the inventive device preferably comprise an electrochemically active material. Preferably, said electrode material is an organic material. More preferably said organic material is a polymer, and may be an electrically conductive polymer. Electrically conductive polymers suitable for use in the device of the invention, are preferably selected from the group consisting of polythiophenes, polypyrroles, polyanilines, polyisothianaphthalenes, polyphenylene vinylenes and copolymers thereof such as described by J C Gustafsson et al. in Solid State Ionics, 69, 145-152 (1994); Handbook of Oligo- and Polythiophenes, Ch 10.8, Ed D Fichou, Wiley-VCH, Weinhem (1999); by P Schottland et al. in Macromolecules, 33, 7051-7061 (2000); Technology Map Conductive Polymers, SRI Consulting (1999); by M Onoda in Journal of the Electrochemical Society, 141, 338-341 (1994); by M Chandrasekar in Conducting Polymers, Fundamentals and Applications, a Practical Approach, Kluwer Academic Publishers, Boston (1999); and by A J Epstein et al. in Macromol Chem, Macromol Symp, 51, 217-234 (1991). In one especially preferred embodiment, the electrically conductive polymer is a polymer or copolymer of a 3,4-dialkoxythiophene, in which said two alkoxy groups may be the same or different or together represent an optionally substituted oxy-alkylene-oxy bridge. It is particularly preferred that the polymer is a polymer or copolymer of a 3,4-dialkoxythiophene selected from the group consisting of poly (3,4-methylenedioxythiophene), poly(3,4-methylenedioxythiophene) derivatives, poly(3,4-ethylenedioxythiophene), poly(3,4-ethylenedioxythiophene) derivatives, poly(3,4-propylenedioxythiophene), poly(3,4-propylenedioxythiophene) derivatives, poly(3,4-butylenedioxythiophene), poly(3,4-butylenedioxythiophene) derivatives, and copolymers therewith.

In one embodiment of the device, said electrically conductive polymer is poly(3,4-ethylenedioxythiophene) (PEDOT). Preferably the electrodes further comprise a polyelectrolyte compound, more preferably said polyelectrolyte compound is poly(styrene sulfonic acid) or a salt thereof. One especially preferred material for use in the electrodes of the device of the invention is poly(3,4-ethylenedioxythiophene) with a poly (styrene sulfonate) polyanion (in the following referred to as PEDOT:PSS). In an embodiment the electrodes are present in the form of a thin layer of PEDOT:PSS deposited on a solid substrate.

The electrodes of the inventive device may further comprise a hydrogel. The hydrogel is preferably based on polymers selected from the group consisting of polyacrylates, such as poly(2-hydroxyethyl methacrylate) and poly(acrylamide), polyelectrolytes, such as poly(styrene sulfonic acid) (PSS) and poly(acrylic acid) (PAA), polysaccharides, such as agarose, chitosan and dextran, gelatin, polyvinyl alcohol, polyvinyl pyrrolidone and polyethylene glycol.

In an embodiment the electrodes are present in the form of a thin layer of PEDOT:PSS deposited on a solid substrate and a thin layer of chitosan deposited on said PEDOT:PSS layer. Other combinations of materials can also be used.

The electrodes are preferably arranged in a common plane on a solid substrate. Preferably the electrodes are deposited onto said substrate by printing or lamination techniques. Use of printing methods in combination with conventional semiconductor processing methods, such as lithography and etching, allows for the electrodes to be patterned with a resolution of about 1 μm. This allows the inventive device to be manufactured in miniature scale, which e.g. is useful in biochemical and cell applications where samples and preparations may be available only in very minute amounts. Preferably the thickness of the electrodes is less than 1 mm. The thickness is measured in a direction normal to the support on which the electrode is arranged.

In an embodiment, the volume of one of the electrodes is made substantially larger compared to the other in order to prevent irreversible oxidation or reduction of that element. For example, the electrode which is to be oxidized is made substantially larger compared to the electrode which is to be reduced, such that the risk of an irreversible oxidation or over oxidation of the first element is minimized or eliminated. The suitable volume ratio between the first and second electrodes depend on the materials used. The volume of the first electrode may e.g. be 3 times larger, or 5 times larger compared to the second electrode. The thickness of the first and the second elements are preferably equal.

An embodiment of the device is provided, in which at least one of the electrodes is biocompatible. The term biocompatible is used herein to characterize a material or a surface allowing cultivation of cells thereon or in close association therewith. Cultivation of cells refers to attachment, maintenance, growth and/or proliferation of said cells. An example of an electrode material according to the invention that provides a biocompatible surface is PEDOT:PSS. The biocompatibility of an electrode allow for studies of cellular activities in cells cultivated on or in close association with the electrode.

Means for Limiting an Electronic Current:

In order for the electrically controlled transport of ions via the ion-conductive channel to be provided, the inventive device comprises means for limiting the electric current across the channel, such that a potential difference can be maintained across the channel. By altering the size of the potential difference across the channel, the amount of transported ions through the channel can be varied.

According to an embodiment of the invention, the electric current is limited by the electron conductivity or resistivity of the channel material, i.e. the material comprised in the ion-conductive channel. In other words, provided that the electron conductivity of the channel material is sufficiently low, a desired potential difference across the channel can be maintained. In this embodiment the electron conductivity of the ion-conductive channel is preferably lower than that of the electrodes. Hence, means for limiting the electronic current between said source and target electrodes comprises a portion of said ion-conductive channel having a reduced electron conductivity, preferably compared to the electron conductivity of said source and target electrodes, respectively.

The inventors have also found that the electron conductivity can be limited by means of a second applied potential. Hence, according to another embodiment of the invention, wherein at least one of the source and target electrodes is made of an electrochemically active material, the electric current is limited by a further voltage applied across a first electrolyte which is in electrochemical contact with said electrochemically active material, such that an electrochemical reaction may occur between the electrolyte and the electrochemical material when a voltage is applies. The two voltages, i.e. the voltage applied to the ion-conductive channel and the voltage applied across the electrolyte, one of the voltages is arranged to cause either an oxidation or a reduction at one of the source and target electrodes and the other voltage is arranged to cause the opposite reaction at the same electrode. More specifically, the first voltage or the channel voltage, applied across the ion-conductive channel, causes an oxidation or reduction of said electrochemically active material, depending on the polarity of the applied channel voltage. In order to facilitate the application of said second voltage, a first electrode is preferably provided, which is in electrostatic or electrochemical contact with said electrolyte. It is not necessary that an electrochemical reaction occurs between the electrolyte and the first electrode in order for a limitation of the electric current to be achieved, provided that the first electrode attracts enough charges when the voltage is applied, e.g. by having a sufficiently lager area. Thus, an electrostatic contact between said first electrode and said electrolyte can be sufficient. However, said first electrode and said electrolyte are preferable in electrochemical contact, such that a respective reduction and an oxidation can occur at the first and second electrodes, respectively.

Thus, means for limiting an electronic current between said source electrode and said target electrode may comprises a first electrode, which first electrode is different from both said source electrode and said target electrode; and a second electrode, which second electrode is one and the same as either said source electrode or said target electrode. Further, the first electrode is in electrostatic or electrochemical contact with a first electrolyte, and the second electrode is in electrochemical contact with the second electrolyte.

According to a first example, the voltage across said ion-conductive channel causes an oxidation at said source electrode, and a second voltage applied across an electrolyte in ionic contact with said source electrolyte causes a reduction at said source electrode. The portion of the electrode between the source and the target electrolyte is normally highly reduced. The exact mechanism behind this local reduction is unclear, but a plausible explanation is that the ion conductivity is higher in the portions of the electrode material which are in contact with an electrolyte. This means that when ion transport is effected, ions may accumulate in the ion-conductive channel, due to the lower ion conductivity there compared to the electrode portions in contact with the electrolyte. The reduction of the ion-conductive channel results in a decrease in electron conductivity of the channel, providing essentially the same effect as an ion-conductive channel comprising a material having an intrinsically low electron conductivity as described above. It should be emphasized, however, that the present invention does not depend on any particular theoretical explanation. Neither does the skilled person need to rely on any particular theoretical foundation in order to carry out the invention.

Below is described two further examples of limiting the electron conductivity by means of an applied potential.

According to a second example, the voltage across said ion-conductive channel causes a reduction at said source electrode, and a second potential applied across an electrolyte in ionic contact with said source electrode causes a oxidation at said source electrode.

According to a third example a voltage across said ion-conductive channel causes a reduction at said target electrode, and a second voltage applied across an electrolyte in ionic contact with said target electrode causes an oxidation at said target electrode.

The above described embodiment facilitates a streamlined low cost production as it allows the same material to be used in electrodes and in the ion-conductive channel. Further, this embodiment allows a dynamically controlled limitation of the electron flow in the ion conductive channel, i.e. a limitation of the electronic current between said first and second electrodes can be varied by altering the electric field applied across said electrolyte.

A yet further embodiment comprises a combination of least two of the embodiments described above. Such an embodiment may for example comprise both an ion-conductive channel having a low electron conductivity, and a further electrode in ionic contact with e.g. either the source electrolyte, target electrolyte or an additional electrolyte. In other words the device comprises at least three electrodes, wherein two are in ionic contact with the same electrolyte.

An embodiment of the invention comprises two or more source electrodes ionically connected to the same target electrode. This configuration provides further advantages in that e.g. two or more different ions can be transported separately to the same target electrolyte, the same ion can be transported from two or more different source electrolytes to the same target electrolyte allowing the rate of transport to be controlled thereby. It also allows for spatially resolved delivery of ions, i.e. the same or different ions can be directed to different areas within the target electrode.

Ion-Conductive Channel:

The ion-conductive channel used in the invention is made of a solid or semi-solid material which is able to conduct ions. According to one embodiment of the invention the ion-conductive channel is essentially electronically non-conductive, i.e. the capability of conducting electrons is substantially limited. When reference is made to the ion-conductive channel being or being rendered "essentially non-conductive" or simply "non-conductive", those terms are intended to encompass completely insulating materials as well as materials which has been rendered sufficiently deactivated and insulating to be useful e.g. as an electrically insulating barrier between areas of the polymer that have not been rendered essentially non-conductive. Such essentially non-conductive polymers have preferably had their conductivity reduced by a factor greater than $10^2$, and even more preferably greater than $10^5$. Thus, to render a polymer essentially non-conductive or to render a polymer non-conductive is, for the purpose of the present invention, to be interpreted as the action of substantially reducing the conductivity of the polymer.

When a voltage is applied across an ion-conductive channel that has a limited electron conductivity, a potential difference between anode and cathode will be maintained. The potential difference generated will effect transport of ions present in the ion-conductive channel or in the ion-conductive electrodes connected to the ion-conductive channel. The mechanism behind the ion transport has not been fully elucidated. It should be pointed out, however, that the present invention does not depend on any particular theoretical explanation. Neither does the skilled person need to rely on any particular theoretical foundation in order to carry out the invention. One driving force for ion transport between the two electrodes are electrochemical reactions in an electrochemically active electrode material, which are effected when a voltage is applied to such a material in contact with an electrolyte. When a conductive polymer, such as PEDOT:PSS, is used as the electrode material and a voltage is applied across the ion-conductive channel the region of the source electrode, which is in contact with the source electrolyte, will be oxidized, and the region of the target electrode, which is in contact with the target electrolyte, will be reduced according to the reaction below.

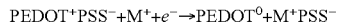

Another driving force for the ion transport is the force imposed on any charged entity present in the electrical field which is created in the ion-conductive channel when a voltage is applied across the channel.

The capability of the ion-conductive channel of being ion-conductive, whilst being essentially electronically non-conductive, may be inherent in the material used. Some materials that could be used as ion-conductors in the ion-conductive channel of the inventive device include polyelectrolytes such as poly(styrene sulfonic acid) (PSS) and poly(acrylic acid) or hydrogels based on polyacrylates, such as poly(2-hydroxyethyl methacrylate) and poly(acrylamide), polyelectrolytes, such as poly(styrene sulfonic acid) (PSS) and poly(acrylic acid) (PAA), polysaccharides, such as agarose and dextran, gelatin and other water soluble polymers, such as polyvinyl alcohol, polyvinyl pyrrolidone, polyethylene glycol and chitosan. Ionic liquids in a semi-solid state could also be used. Other examples of materials which are inherently ion-conductive and essentially electronically non-conductive include conductive polymers such as those mentioned above, which have been overoxidized and thereby rendered electronically non-conductive. In context of this invention an overoxidized state is a non-reversible electronically non-conducting state of the material.

In some embodiments, the material used in the ion-conductive channel may be the same as a material used to facilitate ion transport in the electrodes. For example, the ion-conductive channel may comprise a hydrogel in order to facilitate ion transport.

Preferably the ion-conductive channel comprises an organic material, more preferably said organic material comprises a polymer. The polymer may preferably be a hydrogel based on a polymer selected from the group consisting of polyacrylates, such as poly(2-hydroxyethyl methacrylate) and poly(acrylamide), polyelectrolytes, such as poly(styrene sulfonic acid) (PSS) and poly(acrylic acid) (PAA), polysaccharides, such as agarose and dextran, gelatin and other water soluble polymers, such as polyvinyl alcohol, polyvinyl pyrrolidone and polyethylene glycol. The ion-conductive channel may also comprise a polyelectrolyte, such as for example poly(styrene sulfonic acid) (PSS) or poly(acrylic acid).

In an embodiment of the device according to the invention, the ion-conductive channel comprises an over-oxidized electrically conductive polymer material, preferably over-oxidized poly(3,4-ethylenedioxythiophene):poly(styrene sulfonic acid) (PEDOT:PSS).

In a preferred embodiment of the invention, the ion-conductive channel, which is used to ionically connect the source and target electrodes, comprises the same conductive polymer as that present in said electrodes, with the difference that the conductive polymer present in the ion-conductive channel has been overoxidized, i.e. its electron conductivity has been permanently reduced by means of oxidation.

In another embodiment of the device, said source and target electrodes are two regions of a single conductive polymer layer, separated by a region of said layer which has been overoxidized. In other words, said electrodes and said ion-conductive channel is formed of the same material and arranged as a unitary element.

In a preferred embodiment, the device of the invention is all-organic, i.e. all materials present in the device are organic. One advantage of all-organic devices is that they may be more readily recycled than devices comprising a combination of organic and inorganic materials that may require disassembly prior to recycling.

An inherent advantage of a device according to the invention is the low voltage required to effect ion transport from a source to a target electrolyte.

Magnitude and polarity of the voltages to be applied in the inventive device and method will vary depending on a number of factors, such as choice of electrode material(s), the ion to be transported, the distance over which the ions are transported, etc. The polarity of the applied voltages will easily be selected by a person skilled in the art, taking into account the type of charge (positive or negative) of the ion to be transported. The magnitude of the voltage to be applied may in the light of the present invention easily be determined in order to transport a desired amount of ions.

The voltage applied across the ion conductive channel may for example be within the range of from about 0.1 V to about 100 V. The optimal voltage to apply between electrodes will depend on the characteristics of the polymer used, the electrolyte used, the ion to be transported and the manner in which the voltage is applied to the interface between polymer and electrolyte. However, the voltage is preferably in the range of from 0.1 to 100 V, more preferably in the range of from 0.1 V to 20 V. The inventors have found that ion transport using the inventive device can be further improved by means of an additional electrode, represented herein by a source resetting electrode. The source resetting electrode is used to promote ion transport from the source electrolyte to the target electrolyte. This promotion is effected by means of a voltage applied across the source electrolyte, between the source electrode and a source resetting electrode, which is different from said target electrode and which is in electrostatic or electrochemical contact with said source electrolyte. In the case where the source electrode is of an electrochemically active material, an electrochemical reaction occurs on the surface and/or in the bulk of the electrode in contact with the electrolyte when said voltage is applied. When positive ions are transported the voltage applied across the source electrolyte using said source resetting electrode preferably serves to balance the oxidation of the source electrode, which occurs during ion transport from the source to the target electrode. This prevents overoxidation or complete reduction of said source electrode, which might otherwise result in a deterioration of the ion transport properties of the device. Thus a preferred embodiment of the inventive device further comprises a source resetting electrode, arranged to be in electrochemical contact with said source electrolyte, such that ion transport from the source electrolyte to the target electrolyte is promoted by means of a voltage is applied to said source and source resetting electrodes. The voltage to be applied in this embodiment is preferably within the range of from about 0.1 V to about 10 V.

The inventors have also found that ion transport can be further improved by means of another electrode, represented herein by a target resetting electrode in electrostatic or electrochemical or ionic contact with said target electrode. The voltage applied across the target electrolyte using said target resetting electrode preferably serves to balance the oxidation or reduction of the target electrode, which occurs during ion transport from the source to the target electrode. This prevents said target electrode from becoming completely reduced or overoxidized, which would otherwise result in a deterioration of the ion transport properties of the device. Reoxidation of the target electrode using the target resetting electrode results in a release of ions from the target electrode into the second electrolyte. In an embodiment without the target resetting electrode this release may be effected by means of diffusion.

Thus, in a preferred embodiment, the device according to the invention further comprises a target resetting electrode, arranged to be in electrostatic or ionic contact with said target electrolyte, such that ion transport from the source electrolyte to the target electrolyte is promoted by means of a voltage applied to said target electrode and target resetting electrode. The voltage to be applied in this embodiment is preferably within the range of from about 0.1 V to about 10 V.

In a case where ion transport is promoted by means of a source and/or target resetting electrode the source and target electrodes are not as easily consumed, i.e. completely oxidized or reduced, respectively, since they are regenerated with respect to their respective oxidation states.

In an embodiment of the invention the ion-conductive channel preferably comprises the same ion-conductive material as the electrodes, the material is preferably PEDOT:PSS.

In an embodiment of the invention, the source and target electrodes are ionically connected by an ion-conductive channel formed by selective patterning and overoxidation of PEDOT:PSS leaving an non-overoxidized channel through which ion transport can be effected.

Manufacturing

The ion transport device according to the invention is also particularly advantageous in that it can be easily realized on a support, such as polymer film or paper. Thus, the different components can be deposited on the support by means of conventional printing techniques such as screen printing, offset printing, gravure printing, ink-jet printing and flexographic printing, or coating techniques such as knife coating, doctor blade coating, extrusion coating and curtain coating, such as described in "Modern Coating and Drying Technology" (1992), eds E D Cohen and E B Gutoff, VCH Publishers Inc, New York, N.Y., USA. In the embodiments of the invention that utilize a conductive polymer material in the electrodes and/or ion-conductive channel, this material can also be deposited through in situ polymerization by methods such as electropolymerization, UV-polymerization, thermal polymerization and chemical polymerization. As an alternative to these additive techniques for patterning of the components, it is also possible to use subtractive techniques, such as local destruction of material through chemical or gas etching, by mechanical means such as scratching, scoring, scraping or milling, or by any other subtractive methods known in the art. An aspect of the invention provides such processes for the manufacture of an ion transport device from the materials specified herein.

Thus, in one embodiment of the device, said electrodes and said ion-conductive channel are directly or indirectly attached to a solid support such as glass. According to another more preferred embodiment said electrodes and said ion-conductive channel are directly or indirectly attached to flexible support, such as a support made of or comprising a plastic film or paper.

The ion transport device according to the invention may preferably be encapsulated, in part or entirely, for protection of the device. The encapsulation retains any solvent needed for e.g. the liquid or solidified electrolyte to function, and also keeps oxygen from disturbing the electrochemical reactions in the device. Encapsulation can be achieved through liquid phase processes. Thus, a liquid phase polymer or organic monomer can be deposited on the device using methods such as spray-coating, dip-coating or any of the conventional printing techniques listed above. After deposition, the encapsulant can be hardened for example by ultraviolet or infrared irradiation, by solvent evaporation, by cooling or through the use of a two-component system, such as an epoxy glue, where the components are mixed together directly prior to deposition. Alternatively, the encapsulation is achieved through lamination of a solid film onto the ion transport device. In preferred embodiments of the invention, in which the components of the ion transport device are arranged on a support, this support can function as the bottom encapsulant. In this case encapsulation is made more convenient in that only the top of the sheet needs to be covered with liquid phase encapsulant or laminated with solid film.

The inventive device may also be manufactured using conventional semiconductor processes, such as photolithography and etching. When such methods are used, the electrode material(s) may preferably be deposited onto the substrate using any suitable deposition method, e.g. printing or lamination. The substrate carrying the electrode material(s) may then be patterned using conventional photoresist/etching techniques, e.g. as described in greater detail in Preparatory Example 1. An ion-conductive channel can be obtained e.g. by deposition of a suitable ion-conductive, electronically non-conductive material or otherwise as defined above.

Further Embodiments

According to one preferred embodiment, the ion-conductive channel has an elongated shape, and spatially overlaps said source electrodes and said target electrodes in order to promote ion transport to and from the ion-conductive channel. More preferably said ion-conductive channel has an elongated shape which extends at least from said source electrode to said target electrode. Most preferably, the ion-conductive channel is arranged as a layer. According to one embodiment, the electrodes and ion-conductive channel of the inventive device are arranged in a common plane. Having the electrodes and the ion-conductive channel arranged in a common plane further simplifies production of the device by ordinary printing methods. Thus, the ion transport device according to the invention preferably uses a lateral device architecture. According to one embodiment the ion conductive channels are narrow, e.g. being more than 20 times longer compared to their width.

In an embodiment of the invention, the source and target electrodes are ionically connected by an ion-conductive channel formed e.g. by selective patterning or overoxidation of PEDOT:PSS leaving an non-overoxidized channel through which ion transport can be effected. If the device comprises more than one source electrolyte ionically connected to one target electrolyte, or, alternatively, one source electrolyte connected to more than one target electrolyte, it is preferable that the ion conductive channels connecting the source and target electrodes are electronically insulated from each other, and/or that the channels are spatially separated from each other. According to one embodiment the channels are narrow.

When the ion conductive channels are made of PEDOT:PSS, electronic insulation and spatial separation may be achieved by selectively overoxidizing the PEDOT:PSS material between the channels. In a preferred embodiment at least two narrow channels are formed by selectively overoxidizing the PEDOT:PSS material.

According to another embodiment of the invention, said source and target electrodes, respectively, are in direct physical contact with said ion conductive channel. According to one embodiment of the invention, said source and target electrolytes, respectively, is in direct physical contact with said ion-conductive channel. This has the advantage of facilitating transport of larger molecules between the electrolytes.

The device according to the invention may also present further features, which facilitate use of the device. Such features include for example terminals for connecting a voltage source to the electrodes of the device, means for encapsulating the device in order to make it more robust to handling, and to prevent evaporation or contamination of liquid electrolytes.

When the device is used, a first liquid or solidified electrolyte can advantageously be deposited so that it covers, at least partly, the source electrode, and a second liquid or solidified electrolyte can advantageously be deposited so that it covers, at least partly, the target electrode.

In one embodiment, the electrodes of the device are arranged such that solid or liquid electrolytes may be deposited directly onto the desired electrodes.

Another embodiment of the inventive device further comprises means for retaining a source and target electrolyte on the device, arranged such that the electrolytes are in contact with the desired electrodes. In an embodiment the device comprises means for retaining one of said source and target electrolytes. In another embodiment the device further comprises means for retaining the other of said source and target electrolytes on the device.

In some embodiments the electrolytes may be confined to a certain area of the device by means of one or more physical or chemical confinement methods. The electrolytes may for example be confined by walls or the like arranged on the device surface, by openings in a partial encapsulation of the device as described herein, or by suitable chemical or physical treatment of the device surface, such as rendering the surface partially hydrophobic, e.g. using a fluorinated coating.

In an embodiment, the source and target electrolytes may be retained on the device by means of a container, arranged such that the electrolytes are in contact with the desired electrodes. Said container may preferably be made of glass or a polymer material, but other materials may also be used. The container may be open or partly or fully sealed.

Said means or container for retaining electrolytes on the device are preferably arranged such that said source electrolyte and said target electrolyte are held separate from each other. The surface of said container is preferably biocompatible.

In one embodiment, the device of the present invention further comprises a source and a target electrolyte receiving area, arranged to receive a source and a target electrolyte in such a way that said source electrolyte is brought into contact with said source and source resetting electrode, and said target electrolyte is brought into contact with said target and target resetting electrode.

The device according to the invention may further comprise means for measuring the amount of ions being transported from the source to the target electrode by measuring the current between the source and the target or the target and the target resetting or the source and the source resetting electrode.

In an embodiment of the invention, wherein e.g. protons are transported, the ion transport results in a pH-change in the target electrolyte.

A device according to the invention may be arranged to deliver ions from one electrolyte containing the ion to be transported to more than one receiving electrolyte. This is achieved by patterning the electrodes and ion-conductive channel(s) in different ways and arranging the electrolytes on the patterned electrodes in such a way that ion transport can be achieved between different electrolytes depending on across which electrodes a potential is applied. Such a multiple receiving electrolyte arrangement allows electrically controlled transport of ions from one source electrolyte to more than one receiving electrolyte. Ion transport to the different receiving electrolytes may be performed in parallel or in sequence, and each receiving electrolyte may be addressed individually through individually applied voltages.

In a similar manner a device according to the invention may be arranged to deliver ions from more than one electrolyte containing an ion to be transported to one receiving electrolyte. Such a multiple source arrangement allows electrically controlled transport of different amounts of different ions to one receiving electrolyte. For example, when $Ca^{2+}$ and $K^+$ are present in two different source electrolytes, their time-resolved arrival at the target electrolyte may be controlled by operating subsequently the ion-conductive channels arranged for transport from the respective source electrolytes. As an alternative, a source electrolyte may comprise different ions such that different ions may be transported from one source electrolyte to a target electrolyte. These arrangements allow for a time-resolved transport of different ions. For example, when $Ca^{2+}$ and $K^+$ are present in the same source electrolyte, their time-resolved arrival at the target electrolyte may be controlled by the voltage applied across the ion-conductive channel.

The device of the present invention may be used to create ion concentration gradients close to the target electrode. Such ion concentration gradients may be useful in bioanalytical applications, such as cell signalling studies.

The device of the present invention may be used to create oscillating ion concentrations close to the target electrode. Such oscillating ion concentration gradients mimic natural processes, and may be useful in bioanalytical applications.

As stated above, a second aspect of the present invention relates to an apparatus for transporting ions to or from, respectively, a cell, comprising a device as defined above and a related cell contact site arranged to provide ionic contact between the cell and the target or source electrolyte, respectively.

As stated above, a third aspect of the present invention relates to the use of a device as defined above for transporting ions to or from, respectively, a cell.

A cell contact site may be realized by means of one or more physical or chemical confinement methods. The cell(s) may for example be confined by walls or the like arranged on the device surface, by openings in a partial encapsulation of the device as described herein, or by suitable chemical or physical treatment of the device surface.

In an embodiment, the cell(s) may be retained on the device by means of a container, arranged such that the cell(s) are in contact with the desired electrodes. Said container may preferably be made of glass or a polymer material, but other materials may also be used. The container may be open or partly or fully sealed. In an embodiment of the invention, said apparatus comprises a multiplicity of said devices and their related cell contact sites, the devices and their related cell contact sites preferably being arranged to create a matrix system thereof, wherein each device may be addressed individually for ion transport purposes. An example of an application where such a matrix system would be useful is in microwell plates, as used e.g. for cell culturing and biochemical research. Management of such a matrix system could conveniently be handled by a personal computer.

In an embodiment of the inventive apparatus, each device and its related cell contact site is arranged to provide ionic contact between a single cell and the target or source electrolyte, respectively. Such single cell contact is rendered possible by the small dimensions achievable in the production of the inventive device, cf. above. Thus, according to the present invention it is possible to address a single cell to, or from, which ions are being transported. Such spatially resolved ion transport has not been possible using any prior art technique.

In an embodiment of the inventive apparatus, said ionic contact between the cell and the target or source electrolyte is provided through a disruption in an insulating layer arranged between the cell and the device. Such a disruption would allow for the provision of contact with a selected cell or group of cells only, whereas the insulating layer would inhibit contact with ambient cells in a cell culture or tissue. In turn, the insulating layer may be coated with a biocompatible material so as to facilitate cell cultivation thereon.

In summary, the inventive device can be employed to deliver ions to single cells or cell populations in order to study, regulate and control different aspects of cell signalling, e.g. when cells are subjected to elevated concentrations of a certain ion(s). It should be pointed out that the different opportunities presented for transporting ions to or from a selected group of cells, or even a single cell, provides a major advantage to such applications.

Another advantage of an apparatus or a device according to the present invention is that it can be manufactured using e.g. conventional printing techniques. This allows for development of affordable single-use articles comprising the inventive device or apparatus, e.g. for use in cell communications research or in clinical settings.

Different arrangements of a cell, whether derived from a cell culture, a tissue or elsewhere, in relation to the device are possible while still providing the desired ion transport function. Thus, in one embodiment, said cell is present in the target or source electrolyte, respectively. In such embodiment, the target or source electrolyte, respectively, may comprise cell culture medium if desirable for the maintenance or growth of said cells. It is also possible that the cell is present on said target or source electrode, respectively. A biocompatible electrode may, e.g., be suitable as a support for cultivation of cells.

As stated above, a fourth aspect of the present invention relates to methods of operating devices as defined herein. Thus, the present invention provides a method of operating a device as defined above to effect electrically controlled transport of ions between a source and a target electrolyte, comprising the steps of:

a) providing a source electrolyte comprising the ions to be transported,
b) providing a target electrolyte,
c) bringing the source electrode of the device in contact with the source electrolyte, and bringing the target electrode of the device in contact with the target electrolyte,
d) applying a voltage across the ion-conductive channel of the device, effecting ion transport from the source electrode to the target electrode.

The present invention also provides a method of operating a device as defined above to effect electrically controlled transport of ions between a source and a target electrolyte, comprising the steps of:

a) providing source electrolyte comprising the ions to be transported,
b) providing a target electrolyte,
c) bringing the source electrode and the first electrode of the device in contact with the source electrolyte, and bringing the target electrode of the device in contact with the target electrolyte,
d) applying a first voltage across said first electrode and said source electrode, in order to limit electronic current between said source electrode and said target electrode,
e) applying a second voltage across the ion-conductive channel of the device, effecting ion transport from the source electrode to the target electrode.

The voltage applied in the method is preferably within the range of from about 0.1 V to about 100 V.

Furthermore, in accordance with the invention there is provided a method of operating a device comprising four electrodes as defined above to effect electrically controlled transport of ions between a source and a target electrolyte, comprising the steps of:

a) providing source electrolyte comprising the ions to be transported,
b) providing a target electrolyte,
c) bringing the source electrode and source resetting electrode of the device in contact with the source electrolyte, and bringing the target electrode and target resetting electrode of the device in contact with the target electrolyte,
d) applying a first voltage across the source electrode and source resetting electrode, such that ion transport from the source electrolyte to the target electrolyte is promoted,
e) applying a second voltage across the ion-conductive channel of the device, effecting ion transport from the source electrode to the target electrode, f) applying a third voltage across the target electrode and target resetting electrode, such that ion transport from the source electrolyte to the target electrolyte is promoted.

The first voltage applied in the method is preferably within the range of from about 0.1 V to about 10 V.

The second voltage applied in the method is preferably within the range of from about 0.1 V to about 100 V.

The third voltage applied in the method is preferably within the range of from about 0.1 V to about 10 V.

In one embodiment, said voltages are kept essentially constant.

In another embodiment, said voltages are cycled, i.e. at least one of the voltages is applied intermittently. The other voltages may independently of each other be applied intermittently or constantly. In a preferred embodiment the first voltage is applied constantly, the second and third voltages are applied alternately.

The configuration of the inventive device in some embodiments thereof, allows the device to be manufactured using well known conventional deposition methods, such as printing methods. This is of course very advantageous in that it enables high volume production at relatively low cost, which e.g. allows implementation of the device in affordable single use products.

DETAILED DESCRIPTION OF PREFERRED EMBODIMENTS

The embodiments described below are merely examples of possible device architectures and the present invention should not be limited thereto. The scope of the invention is as defined by the appended claims.

Embodiment 1

Figure 1:
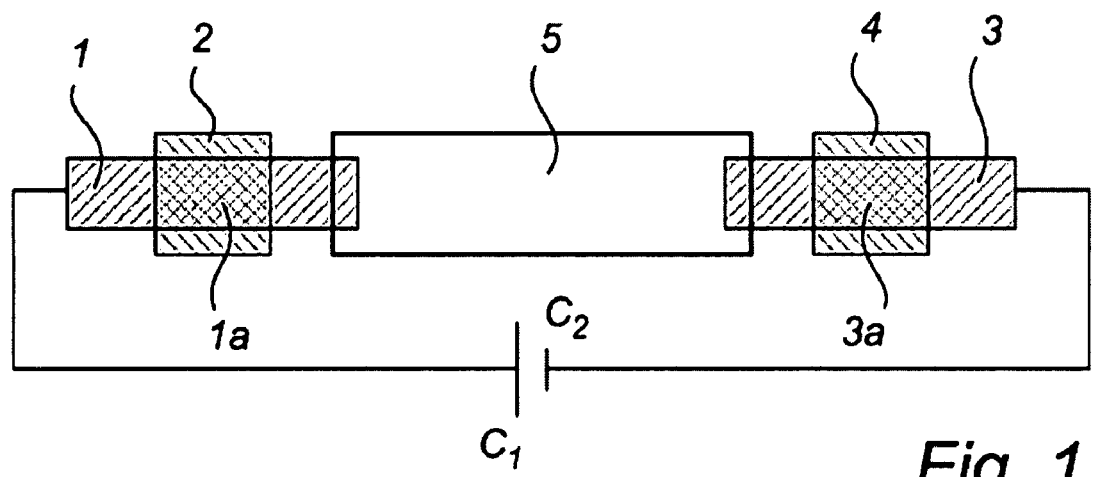
FIG. 1 schematically shows an embodiment of the invention having two electrodes and an ion-conductive channel of low electronic conductivity.

A schematic top-view of an ion transport device according to the invention is shown in FIG. 1. According to this embodiment device comprises a source electrode 1 and a target electrode 3, each capable of conducting ions and electrons. Said electrodes 1,3 have an elongated shape, are preferably arranged as layers and at a distance from each other, i.e. are not in direct physical contact with each other. A portion 1a of the source electrode 1 is in ionic contact with a portion of a source electrolyte 2, and a portion 3a of the target electrode 3 is in ionic contact with the target electrolyte 4. In other words, ions can be transported from said source electrolyte into said source electrode, and transported from said target electrode to said target electrolyte, respectively, by means of diffusion. According to one embodiment of the invention said electrolytes 2,4 are in direct physical contact with the respective electrode 1,3, and according to another embodiment a material capable of conducting ions is arranged between the electrode and the respective electrolyte.

The device further comprises an ion-conductive channel 5 which ionically connects the electrodes 1,3. In other words, the ion-conductive channel 5 provides ionic contact between said source electrode 1 and said target electrode 3. The ion-conductive channel 5 is preferably arranged as a layer which optionally has an elongated shape extending from said source electrode 1 to said target electrode 3. Further, said ion-conductive channel overlaps a portion of said source electrode 1 and a portion of said target electrode 3 in order to facilitate ionic transport between the electrode and the ion-conductive channel. The ion-conductive channel is made of a material having low electronic conductivity, such that when a first potential C1 is applied to said source electrode 1 and a second potential C2 is applied to said target electrode 3, a potential difference |C1−C2| can be maintained across said ion-conductive channel.

During use, transport of ions from said source electrolyte 2 into the source electrode 1, as well as ion transport from the target electrode 3 into a target electrolyte 4 is effected by means of diffusion.

The electrodes 1,3 are connected to a variable power supply, from which a potential across the two electrodes can be applied and varied. When a voltage or potential difference is applied across the ion-conductive channel, ion transport from the source to the target electrode is effectuated. In this embodiment, a higher potential C1 is applied to said source electrode compared to the potential C2 applied to the target electrode. Hence, positive ions will be transported from said source electrode 1 to said target electrode 3.

Embodiment 2

Figure 2:
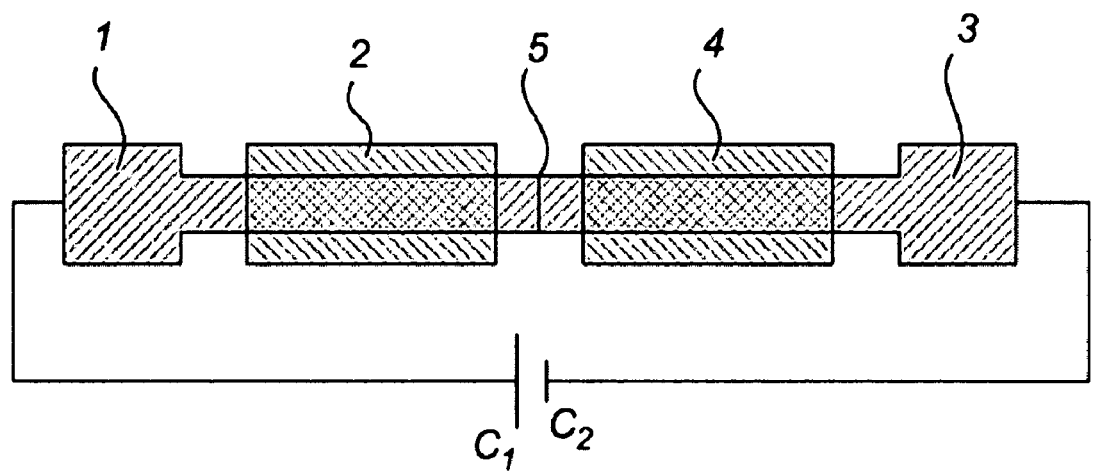
FIG. 2 schematically shows an embodiment of the invention having two electrodes and an overoxidized channel.

A second embodiment of the invention is schematically illustrated in FIG. 2. This embodiment is arranged as described in relation to FIG. 1, except that the source electrode 1, target electrode 3 and ion conductive channel 5 is made of a unitary piece of electrically conductive polymer material, wherein the ion-conductive channel 5 has been formed by rendering a portion of the polymer material electrically non-conducting, or at least essentially non-conducting by means of e.g. overoxidation, which portion is arranged between said source electrode 1 and said target electrode 3. In FIG. 2 the ion-conductive channel is illustrated as a thin line, but the length of the ion-conductive channel, as taken from said source electrode to said target electrode, can also be substantially longer.

Embodiment 3

Figure 3:
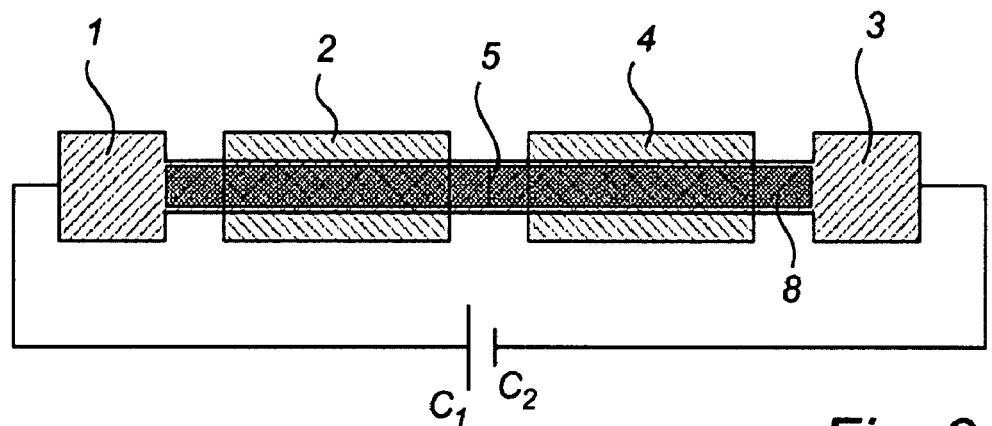
FIG. 3 schematically shows an embodiment of the invention having two electrodes and an overoxidized channel and a hydrogel layer arranged on top of the first and second electrodes.

A third embodiment of the invention is schematically illustrated in FIG. 3. This embodiment is arranged as described in relation to FIG. 1 or 2, except that the ion conductive channel 5, the source electrode 1 and the target electrode 3 further comprises layer of a polymer hydrogel 8, which is arranged between the electrically conductive materials of the electrodes and a respective portion of the source and target electrolytes, such that in ionic contact between the source and target electrolyte and said respective portion of the polymer hydrogel is provided. The hydrogel layer increases ion transport from the first to the second electrolyte by providing an easily accessible pathway for ion transport.

Embodiment 4

Figure 4:
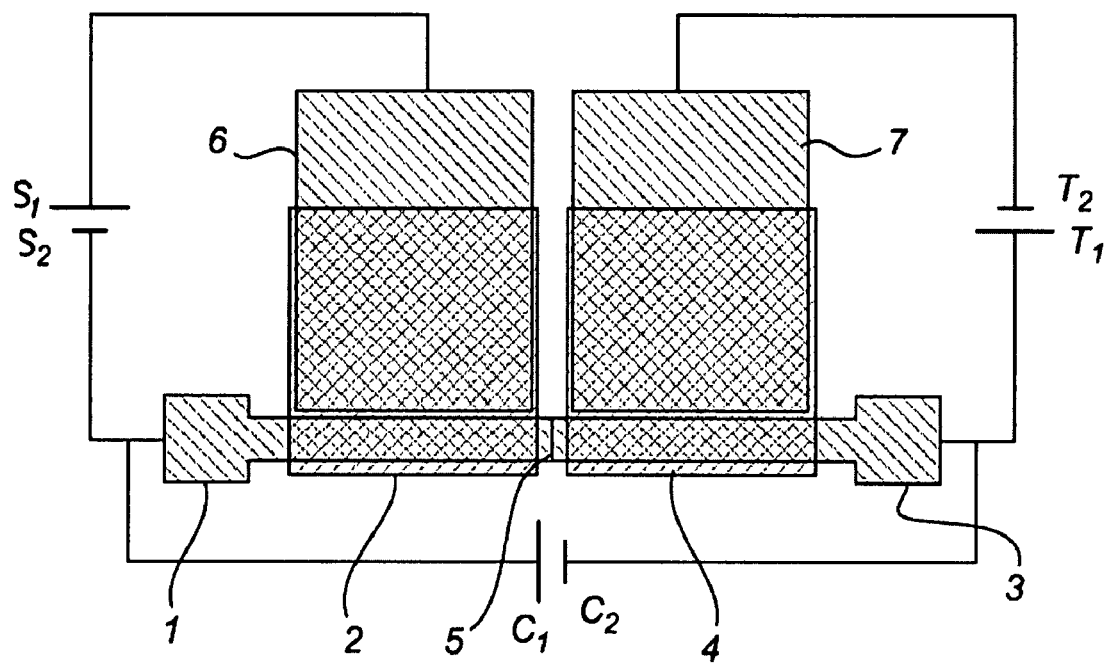
FIG. 4 schematically shows an embodiment of the invention having four electrodes and an overoxidized channel.

A fourth embodiment of the invention is schematically illustrated in FIG. 4. FIG. 4 provides a top-view of a device according to the invention. The basic structure of the device, i.e. the source and target electrodes 1,3 and the ion-conductive channel 5 are arranged as described in relation to FIG. 1, 2 or 3. According to this embodiment of the invention the device further comprises a source resetting electrode 6 and a target resetting electrode 7, physically separated from each other and from said source 1 and target electrodes 3. Preferably, the size of said source and target resetting electrodes 6,7, respectively, is larger than the size of said source and target electrode, respectively. Further, said four electrodes are preferably arranged as layers and possibly arranged in a common plane. Furthermore, said source electrolyte 2 is arranged in ionic contact with said source resetting electrode, and said target resetting electrode 7 is arranged in ionic contact with said target electrolyte 4. Preferably, the separation between the source resetting electrode and the source electrode, and separation between the target resetting electrode and the target electrode is small. All electrodes are connectable to a variable power supply, by which potentials across the different electrodes can be applied independently. As an example, during use, a channel voltage |C–C2| may be applied across the ion-conductive channel by applying a first potential C1 to said a source electrode 1 and a second potential C2 to said target electrode 3, wherein said first potential C1 is higher than said second potential C2. A source voltage |S1–S2| may be applied across the source electrolyte 2 by applying a third potential S1 to said source resetting electrode 6 and a fourth potential S2 to said source electrode 1, wherein said third potential S1 is higher than said fourth potential S2 and said first potential C1 preferably is substantially equal to said fourth potential S2. A target voltage |T1–T2| may be applied across the target electrolyte 4 by applying a fifth potential T1 to said target electrode 3 and a sixth potential T2 to said target resetting electrode 7, wherein said fifth potential T1 is higher than said sixth potential T2, and said second potential C2 preferably is substantially equal to said fifth potential T1. The source voltage |S1–S2| serves to prevent overoxidation of the source electrode 1 and to promote transport of ions from the source electrolyte 2 into the ion-conductive material of the source electrode 1. The channel voltage |C1–C2| serves to transport ions present in the source electrode 1 through the ion-conductive channel 5 into the second ion-conductive electrode 3. The target voltage |T1–T2| serves to prevent the target electrode 3 from becoming completely reduced by reoxidizing it, whereby ions present in the target electrode 3 are released into the target electrolyte 4.

Embodiment 5

Figure 5:
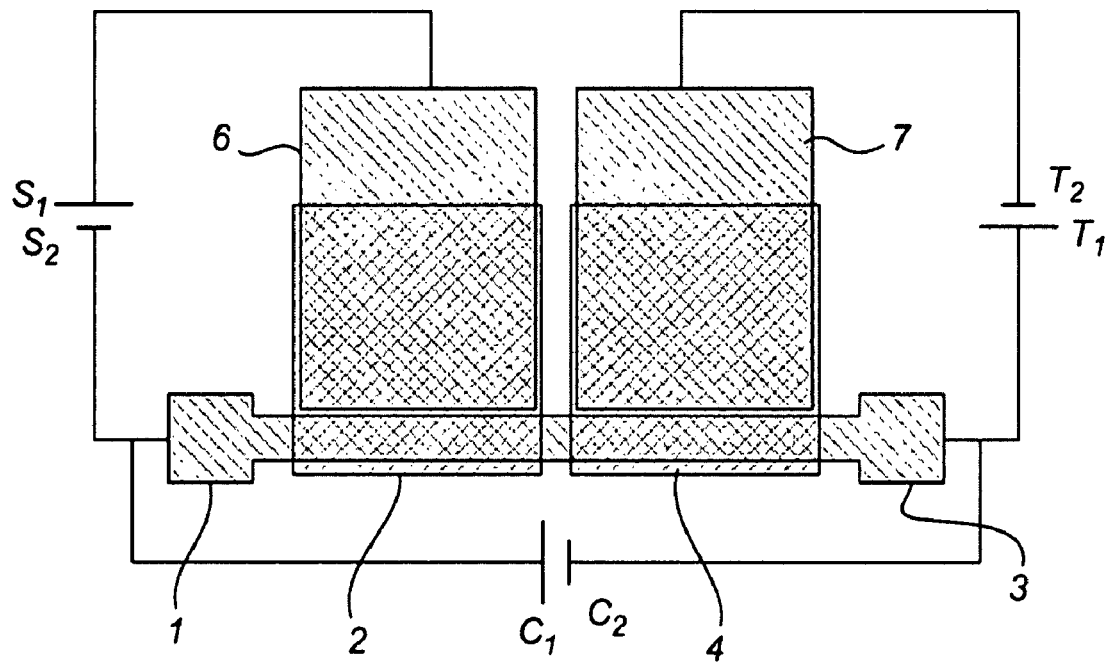
FIG. 5 schematically shows an embodiment of the invention having four electrodes and no overoxidized channel.

A fifth embodiment of the invention is schematically illustrated in FIG. 5. FIG. 5 provides a top-view of a device according to the invention. The device is arranged as described in relation to FIG. 4, except that said ion-conductive channel has the same electron conductivity as said source electrode 1 and said target electrode 3. Preferably, said source and target electrodes and said ion-conductive channel constitutes different parts of a unitary piece of material. In FIG. 5 the ion-conductive channel comprises the part between the source electrode 2 and the target electrode 4 which is not covered by electrolyte. When a source voltage |S1–S2| is applied across the source electrode 1 the electron conductivity of the ion-conductive channel is limited as described above.

Embodiment 5

Figure 15:
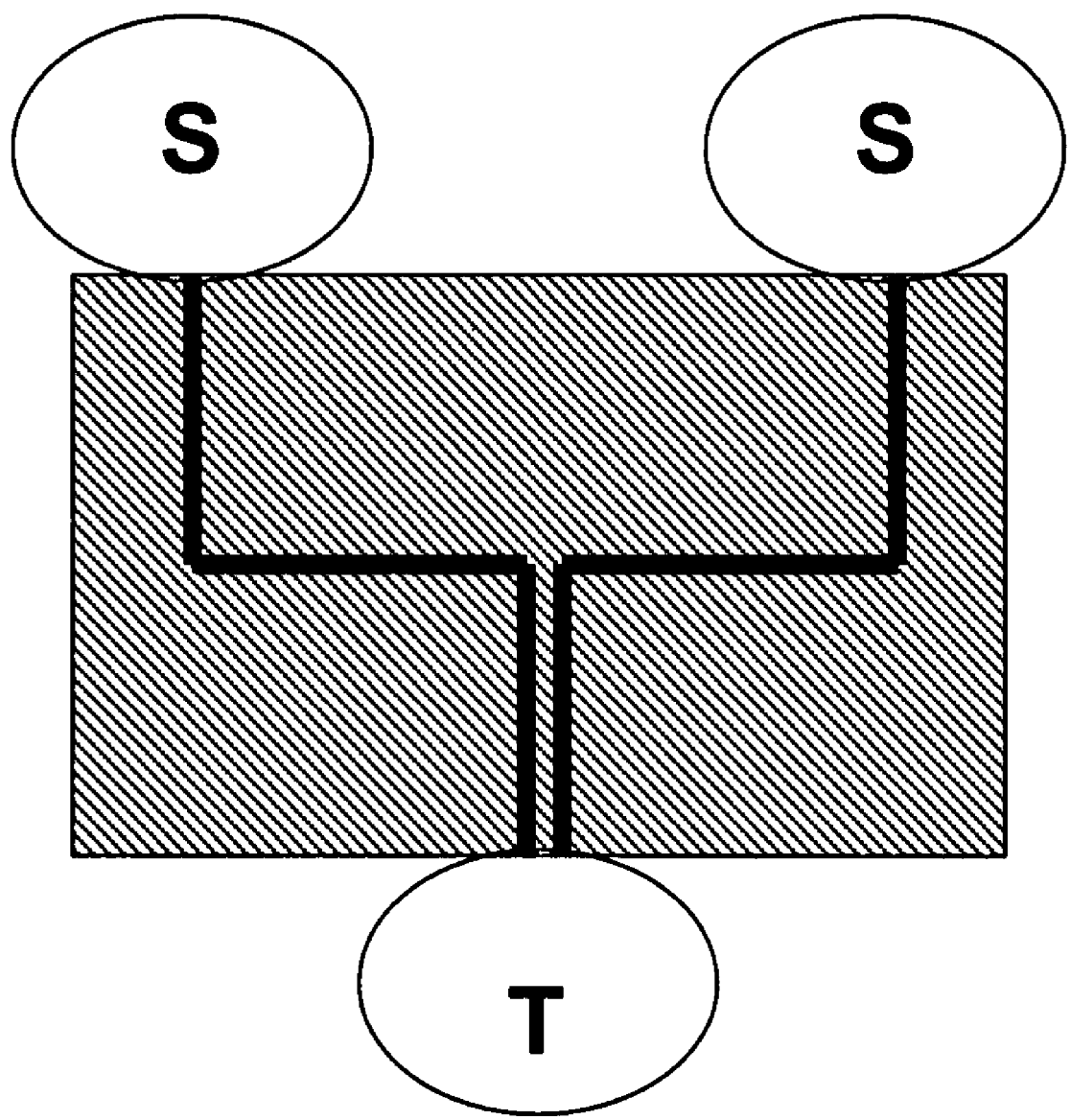
FIG. 15 shows a schematic view of a configuration which is advantageous when one electrolyte is connected to two or more electrolytes.

A schematic top view of a configuration which is advantageous when one electrolyte is connected to two or more electrolytes, or vice versa, is shown in FIG. 15. S denotes source electrode and T denotes target electrode, the shaded area is overoxidized PEDOT:PSS and the bold lines are the non-overoxidized ion transport channels. The ion transport in a respective channel is effectuated by providing a potential difference across said channel.

EXAMPLES

Preparatory Example 1

General Procedure for Fabrication of the Ion Transport Device

Devices were fabricated in a class 1000 cleanroom using photolithographic techniques and dry etching. Devices were conditioned in de-ionized water for 24 hours before use. A general procedure for fabrication of the ion transport devices is shown below.

As substrate, an Orgacon foil (AGFA) was used. Orgacon is a laminate consisting of a first layer of a polyester base and a second layer of PEDOT:PSS.

The Orgacon foil substrate was cleaned by washing in acetone followed by washing in water. The substrate was then baked at 110° C. for 5 min in order to dry the substrate before the etch process step below.

The photoresist (S1818 Microposit) was spin coated onto the Orgacon foil substrate. The photoresist was exposed using a mask-aligner (Suss Microtech MA 6/BA 6). Development was done with a Microposit MF319 developer. The non-covered areas of PEDOT:PSS were etched away using a reactive ion plasma consisting of $O_2$ and $CF_4$. The non-etched photoresist was removed using a Microposit remover 1112A.

A layer of SU-8 (Microchem SU-8 2010) was spin-coated onto the patterned PEDOT:PSS. The SU-8 layer was baked by ramping the temperature from 50° C. to 110° C. during 16 minutes. The SU-8 layer was exposed using a mask-aligner (Suss Microtech MA 6/BA 6). A post-baking step was performed at 110° C. for 6 minutes. The SU-8 layer was developed using an XP SU-8 developer from Micro Resist Technology. The SU-8 layer was patterned in order to define areas for the electrolytes.

Preparatory Example 2

Fabrication of an Ion Transport Device with a Thicker Layer of PEDOT:PSS

The device in this example was fabricated as the device in Preparatory Example 1 except that a thicker layer of PEDOT:PSS was obtained by spin-coating (at 1500 rpm) an additional layer of PEDOT:PSS prior to the masking and etching step. In this case a solution of Orgacon ICP 1010 mixed with 5% diethylene glycol and 0.1% zonyl was used. Spin-coating was followed by a baking step at 110° C. for 10 minutes.

Preparatory Example 3

Fabrication of an Ion Transport Device Having an Overoxidized Line

The device in this example was fabricated as the device in Preparatory Example 1, except that overoxidation of the ion transport channel was performed after the step of stripping the Microposit and prior to the step of applying the SU-8 layer. Overoxidation was performed as follows.

Another layer of photoresist was patterned in order to create opening where PEDOT:PSS was to be over-oxidized. In the opening defined by the patterned photoresist, a 10 mM electrolyte solution of sodium sulphate was placed. Overoxidation was performed by connecting a positive potential to the PEDOT:PSS layer and a negative potential to an external electrode located in the electrolyte. The potential difference used between the PEDOT:PSS layer and the electrode was 20 V. The Microposit remover 1112A was used to remove the photoresist.

Example 1

Ion Transport in a Two-Electrode Device

The experiment was performed in a device fabricated as described in Preparatory Example 1 and as generally described in FIG. 2, comprising two PEDOT:PSS transport electrodes, source and target (1 and 3 in FIG. 2), separated by an ion-conductive channel in the form of an overoxidized line in the PEDOT:PSS obtained as described in Preparatory Example 3.

1.2 ml of a source electrolyte consisting of 0.1 M potassium acetate was deposited onto the device in such a way that it was brought into contact with the target electrode (1). 1.2 ml of a target electrolyte consisting of 1 mM calcium acetate was deposited onto the device in such a way that it was brought into contact with the target electrode (3). The electrolytes were physically separated from each other as well as from the overoxidized line (5) separating the source and the target electrodes.

Figure 6:
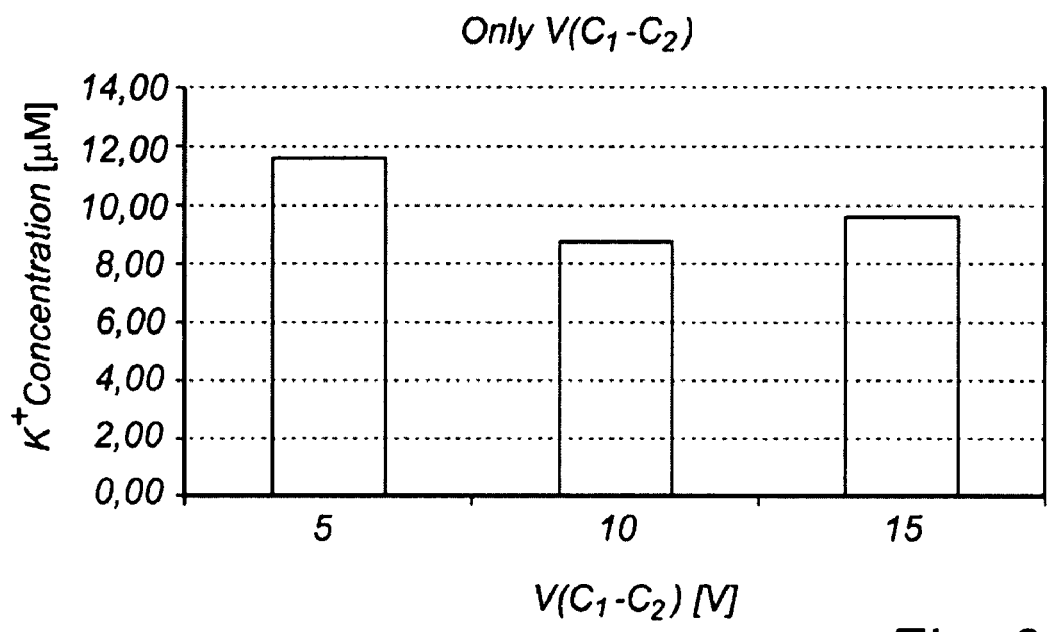
FIG. 6 shows a graph indicating $K^+$ ion transport achieved in Example 1.

Ion transport from the source to the target electrolyte was performed by application a voltage between the source and the target electrodes, across the ion-conductive channel of the device. Three different voltages, 5, 10 and 15 V were applied. The resulting increase in $K^+$ ion concentration in the target electrolyte is presented in FIG. 6.

Example 2

Transport of $K^+$ Ions in a Four Electrode Device Using Cycled Potentials

The experiment was performed in a device fabricated as described in Preparatory Example 1 and as generally described in FIG. 4, comprising two transport electrodes, source and target (1 and 3 in FIG. 4), separated by an ion-conductive channel in the form of an overoxidized line obtained as described in Preparatory Example 3. The device which was used in the experiment further comprised two resetting electrodes, source resetting and target resetting (6 and 7 in FIG. 4).

1.2 ml of a source electrolyte consisting of 0.1 M potassium acetate was deposited onto the device in such a way that it was brought into contact with the source electrode (1) and the source resetting electrode (6). 1.2 ml of a target electrolyte consisting of 1 mM calcium acetate was deposited onto the device in such a way that it was brought into contact with the target electrode (3) and the target resetting electrode (7). The electrolytes were physically separated from each other as well as from the overoxidized line (5) separating the source and the target electrode.

Ion transport from the source to the target electrolyte was performed by application of different potentials to the different electrodes of the device. A constant potential $|S1-S2|=3$ V was applied across the source electrode and the source resetting electrode in order to prevent overoxidation of the source electrode. In order to investigate the ion transport at different potentials across the source and target electrodes, three different potentials $|C1-C2|=0$, 10 and 20 V were applied across the source and target electrode. A potential $|T1-T2|$ of 1 V across the target electrode and the target resetting electrode was applied in order to reoxidize the target electrode and to release the transported ions from target electrode into the target electrolyte. $|C1-C2|$ and $|T1-T2|$ were applied in a sequence, wherein $|C1-C2|$ was first applied for 14 seconds and $|T1-T2|$ then applied for 1 second. This sequence was repeated 40 times resulting in a total time of 10 minutes. Control experiments were performed using de-ionized water as both source and target electrolyte.

Figure 7:
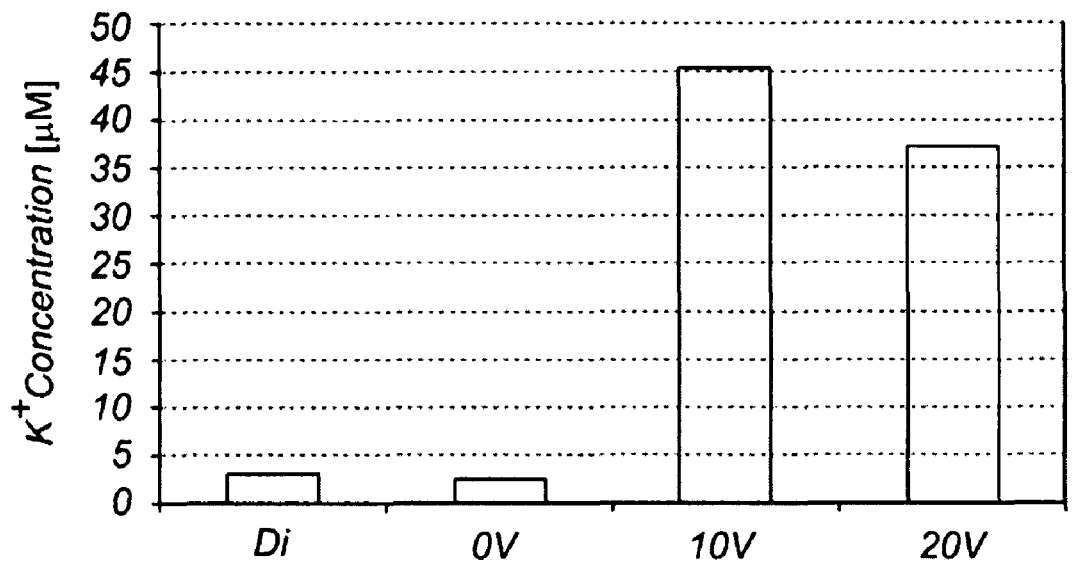
FIG. 7 shows a graph indicating $K^+$ ion transport achieved in Example 2.

The potassium concentration of the target electrolyte was monitored using atomic absorption spectroscopy. 1 ml samples of the target electrolyte were removed and diluted 1:5 with de-ionized water before analysis with atomic absorption spectroscopy. The results of the measurements are shown in FIG. 7.

Example 3

Transport of $K^+$ Ions Using Cycled Potentials and No Overoxidized Line

Figure 8:
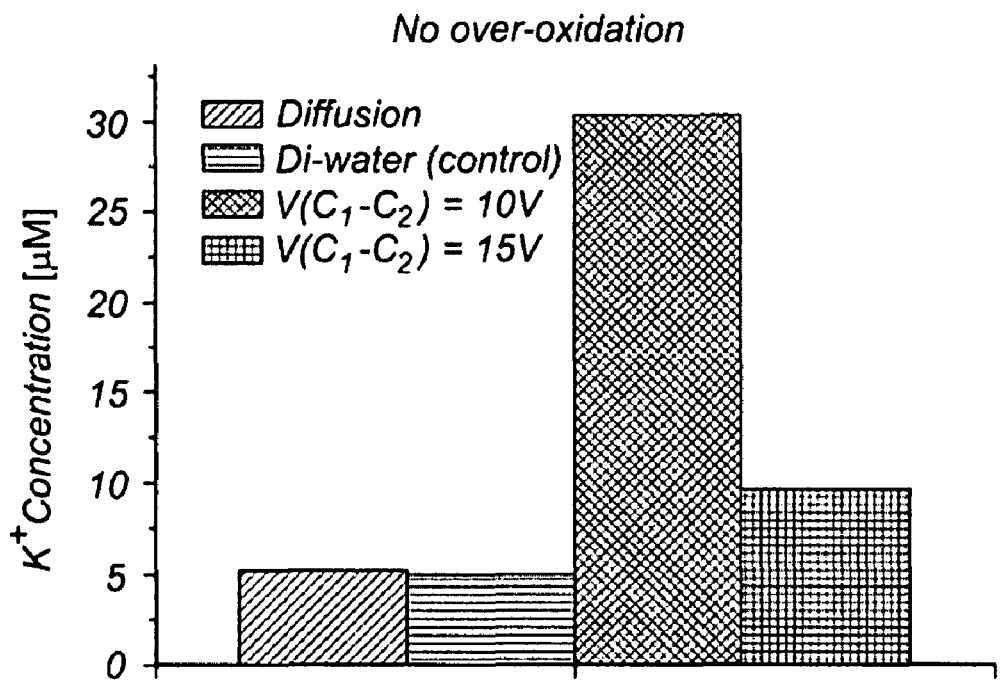
FIG. 8 shows a graph indicating $K^+$ ion transport achieved in Example 3.

The experiment was carried out according to the procedure described in Example 1, with the exception that the device used in this experiment was fabricated according to Preparatory Example 1, i.e. the device did not have the overoxidized line separating the source and target electrodes (1 and 3 in FIG. 5). The voltages $|S1-S2|$, $|C1-C2|$ and $|T1-T2|$ that were used were $|S1-S2|=2$ V, $|C1-C2|=10$ and 15 V and $|T1-T2|=1$ V. When $|C1-C2|$ was 10 V, $|C1-C2|$ was first applied for 7 seconds and $|T1-T2|$ then applied for 3 seconds. When $|C1-C2|$ was 15 V, $|C1-C2|$ was first applied for 8 seconds and |T1−T2| then applied for 2 seconds. This sequence was repeated for a total time of 10 minutes. The results of this experiment are shown in FIG. 8.

Example 4

Transport of $K^+$ Ions Using Constantly Applied Potentials

Figure 9:
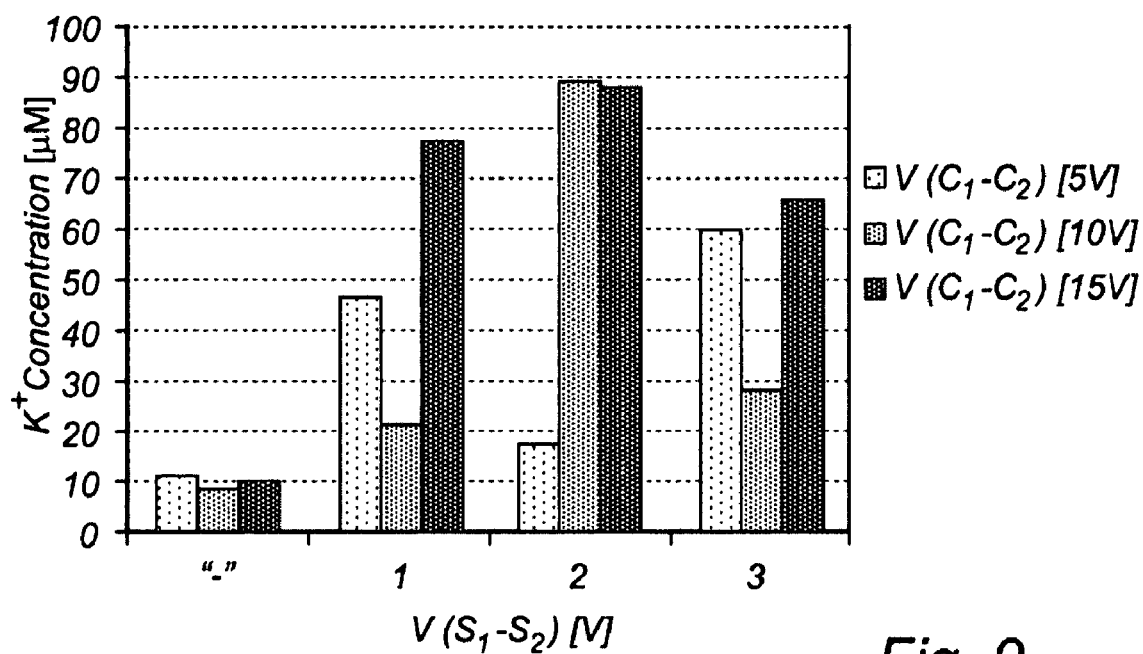
FIG. 9 shows a graph indicating $K^+$ ion transport achieved in Example 4.

This experiment was performed in order to determine if it is possible to transport ions in the inventive device using constantly applied potentials instead of periodically applied potentials as described in example 2. The experiment was performed as Example 2, with the exception that the voltages |S1−S2|, |C1−C2| and |T1−T2| were kept constant at |S1−S2|=0, 1, 2 and 3 V, |C1−C2|=5, 10 and 15 V and |T1−T2|=1 V. Each set of voltages was applied constantly for 10 minutes, after which the potassium concentration in the target electrolyte was determined as described in Example 2. The results of this experiment are shown in FIG. 9.

Example 5

Transport of $K^+$ Using Ion Transport Device Leads to De-Polarization of the Cell Membrane and $Ca^{2+}$ Influx in HCN-2 Neuronal Cells The aim of this example was to demonstrate the transport of $K^+$ ions using an ion transport device according to the invention in order to affect cells growing in the target electrolyte. In biological applications a strict control of $K^+$ level is essential as it is of importance to the resting membrane potential of the cells. A high extracellular concentration of $K^+$ de-polarizes the cell membrane, which in turn activates biological processes in the cell. One of these processes is the activation of voltage operated calcium channels (VOCC's), which senses membrane de-polarization and opens for extracellular $Ca^{2+}$ to enter the cell.

In this example HCN-2 neuronal cells were used. The ion transport device used was manufactured according to preparatory example 3.

Ion transport devices were rinsed with EtOH and conditioned in $dH_2O$ overnight. The following day, HCN-2 cells were seeded on the target electrolyte area (4). A droplet (100 μl) of cell medium (Sigma D6546) was kept on the target electrolyte area (4) to maintain growth and viability of the cells. The cells were then allowed to adhere and grow on the surface over night at 37° C. in a humidity chamber to prevent vaporization of the small volume of cell medium at the target electrolyte area (4). The following day, the target electrolyte (4) cell medium was exchanged with cell medium containing 2 μM Fura-2 AM $Ca^{2+}$ fluorescent marker for 1 hour, then rinsed with cell medium without Fura-2 AM and analysed on the microscope. To obtain as high $K^+$ concentration as possible in the target electrolyte (4), a micro-chamber containing ~10 μl cell medium was created with thin plastic foil over the target electrolyte (4) and sealed with silicon grease. Electrolyte consisting of 0.1 M KCl or 0.1 M NaCl or $dH_2O$ was placed on the source electrolyte area (2) as denoted below. Voltages were applied between the source and the target electrodes (10 V), the source and the source resetting electrodes (1 V) and the target and the target resetting electrodes (1 V) as denoted below.

Figure 10A:
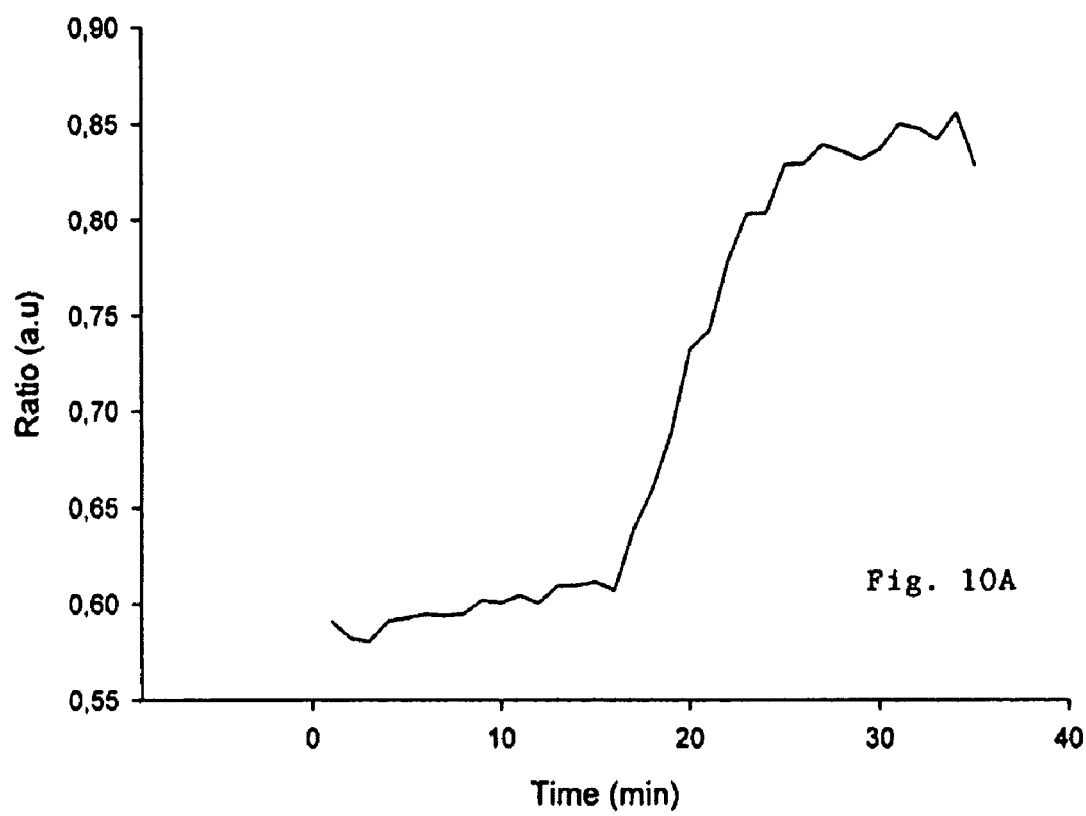
FIGS. 10 A-F are graphs representing ratios of intracellular $Ca^{2+}$ (in arbitrary units) in HCN-2 cells as a function of time, the results of Example 5.

HCN-2 Cells Respond in Intracellular $Ca^{2+}$ Upon Stimulation with Transported $K^+$ A. The ion transport device was started after 4 min. Source electrolyte (2) was 0.1 M KCl. A voltage of 10 V was applied between the source and the target electrodes only. Cell medium started to dry out after 35 min. FIG. 10A shows a clear increase in intracellular $Ca^{2+}$ after 15 min. The ion transport device had been active for 11 min. before onset of the response.

Figure 10B:
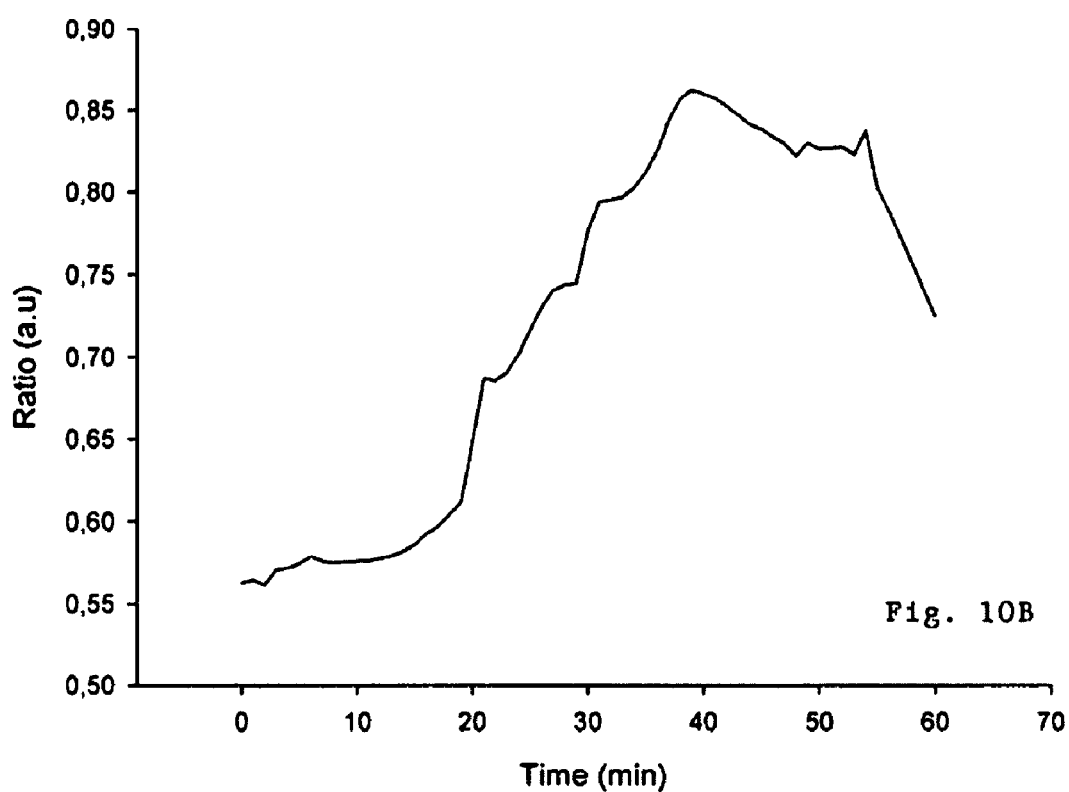

B. The ion transport device was started after 3 min. Source electrolyte (2) was 0.1 M KCl. A voltage of 10 V was applied between the source and the target electrodes only. Cell medium started to dry out after 60 min. FIG. 10B shows a clear increase in intracellular $Ca^{2+}$ after 15 min. The ion transport device had been active for 12 min. before onset of the response.

Figure 10C:
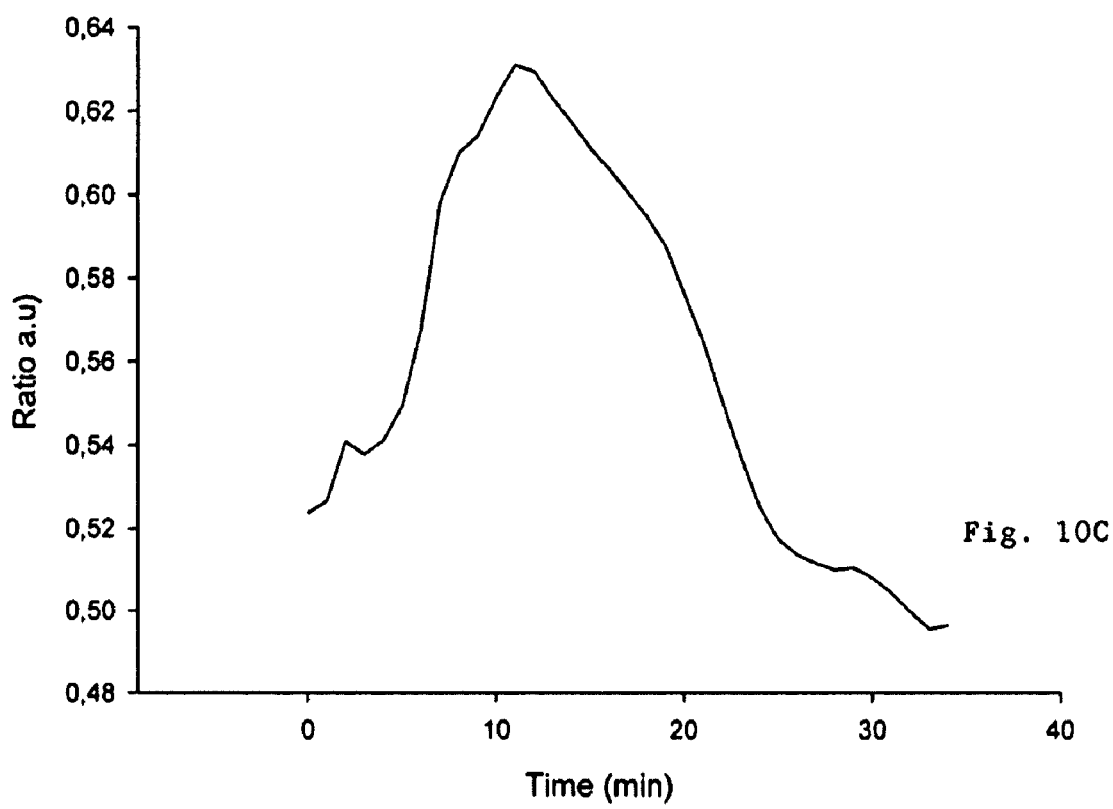

C. The ion transport device was started after 2 min. Source electrolyte (2) was 0.1 M KCl. A voltage of 10 V was applied between the source and the target electrodes and voltages of 1 V were applied between the source and the source resetting electrode and between the target and the target resetting electrode, respectively. Cell medium started to dry out after 35 min. FIG. 10C shows a weaker but faster increase in intracellular $Ca^{2+}$ after 5 min. The ion transport device had been active for 3 min before onset of the response.

HCN-2 Cells do not Respond Upon Stimulation with Transported Na+ or $dH_2O$

Figure 10D:
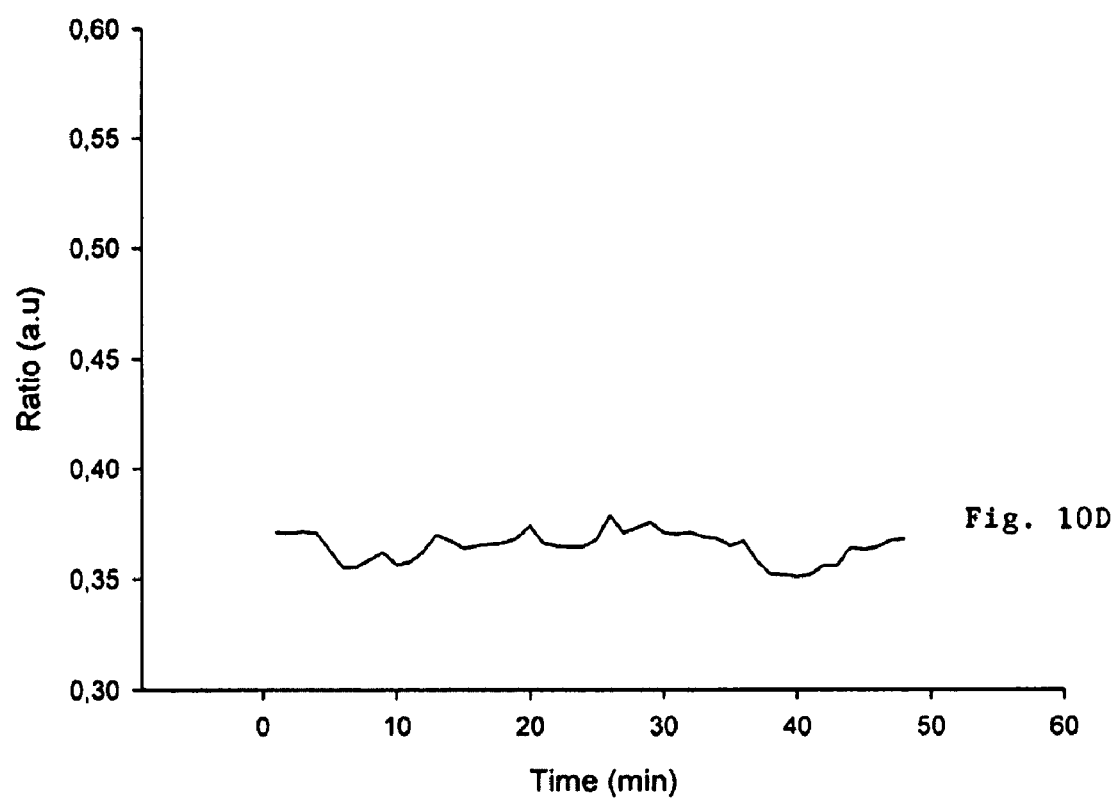

D. The ion transport device was started after 3 min. Source electrolyte (2) was 0.1 M NaCl. A voltage of 10 V was applied between the source and the target electrodes and voltages of 1 V were applied between the source and the source resetting electrode and between the target and the target resetting electrode, respectively. Cell medium started to dry out after 50 min. FIG. 10D shows no increase in intracellular $Ca^{2+}$ upon stimulation with transported $Na^+$.

Figure 10E:
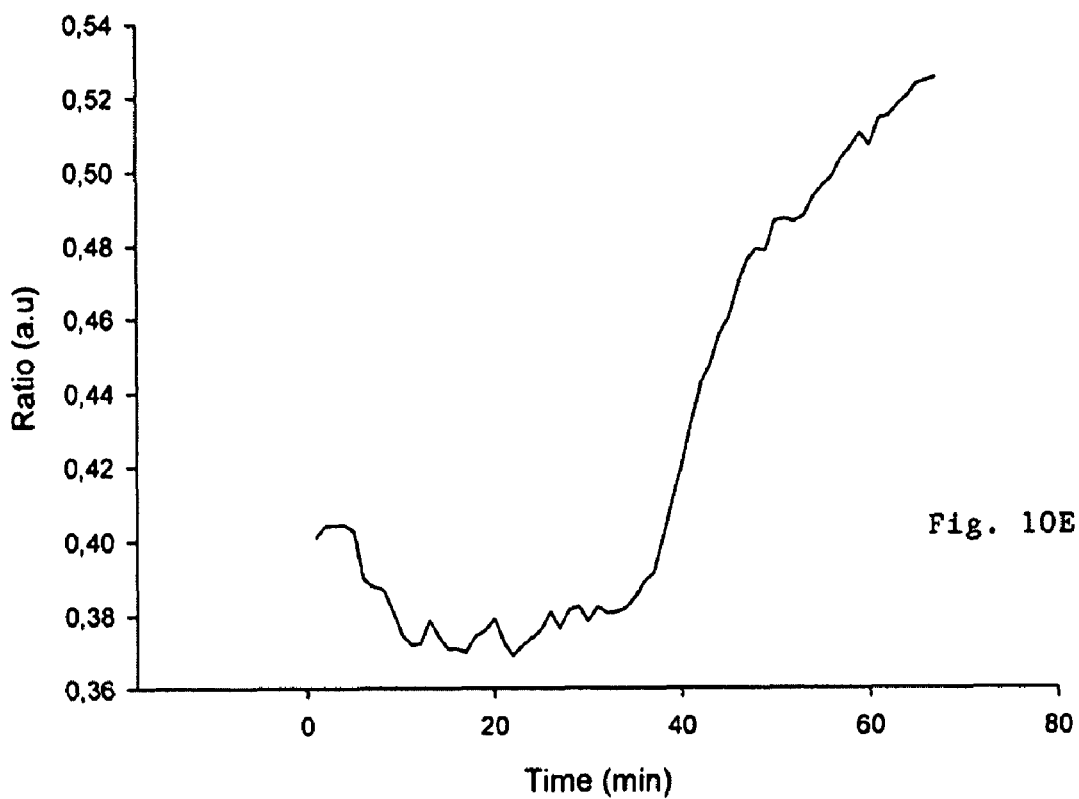

E. The ion transport device was started after 4 min. Source electrolyte (2) was 0.1 M NaCl. A voltage of 10 V was applied between the source and the target electrodes and voltages of 1 V were applied between the source and the source resetting electrode and between the target and the target resetting electrode, respectively. Cell medium started to dry out after 65 min. After 35 min ~50 mM KCl was added to the microchamber. FIG. 10E shows no increase in intracellular $Ca^{2+}$ upon stimulation with transported $Na^+$, but a clear increase is shown after manual addition of $K^+$ using a pipette.

Figure 10F:
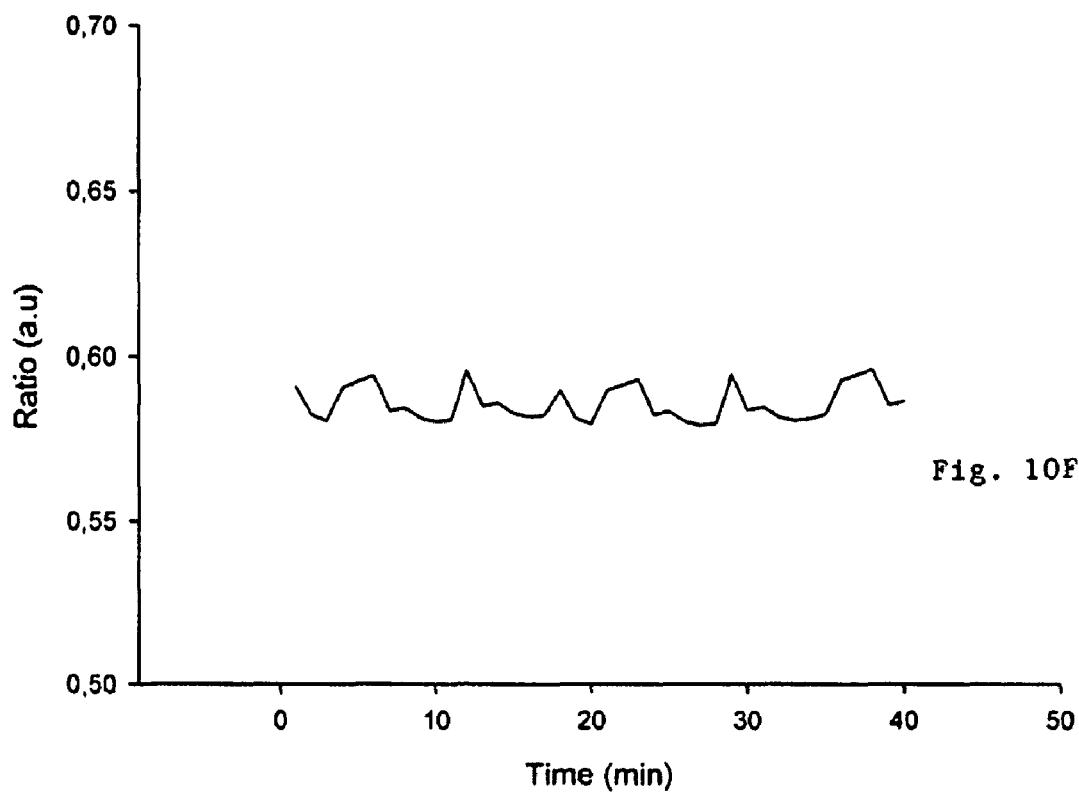

F. The ion transport device was started after 5 min. Source electrolyte (2) was $dH_2O$. A voltage of 10 V was applied between the source and the target electrodes and voltages of 1 V were applied between the source and the source resetting electrode and between the target and the target resetting electrode, respectively. Cell medium started to dry out after 40 min. FIG. 10F shows no increase in intracellular $Ca^{2+}$ when using $dH_2O$.

Hence, it was shown that HCN-2 neuronal cells responded in intracellular $Ca^{2+}$ upon stimulation with $K^+$ transported using an ion transport device according to the invention. Control experiments where $Na^+$ ions were transported to the cells did not result in $Ca^{2+}$ response, which indeed shows that the triggered $Ca^{2+}$ response is $K^+$ dependant. The swift response seen in the cells indicates that the cells are subjected to a locally high concentration of $K^+$ and that this is mediated directly from the polymer to the cell rather than as a result of increasing concentration in the target electrolyte cell medium.

Example 6

Characterization of the Ion Transport Device

In order to further characterize the ion transport device manufactured according to Preparatory example 3, the following experiments were performed.

Figure 11:
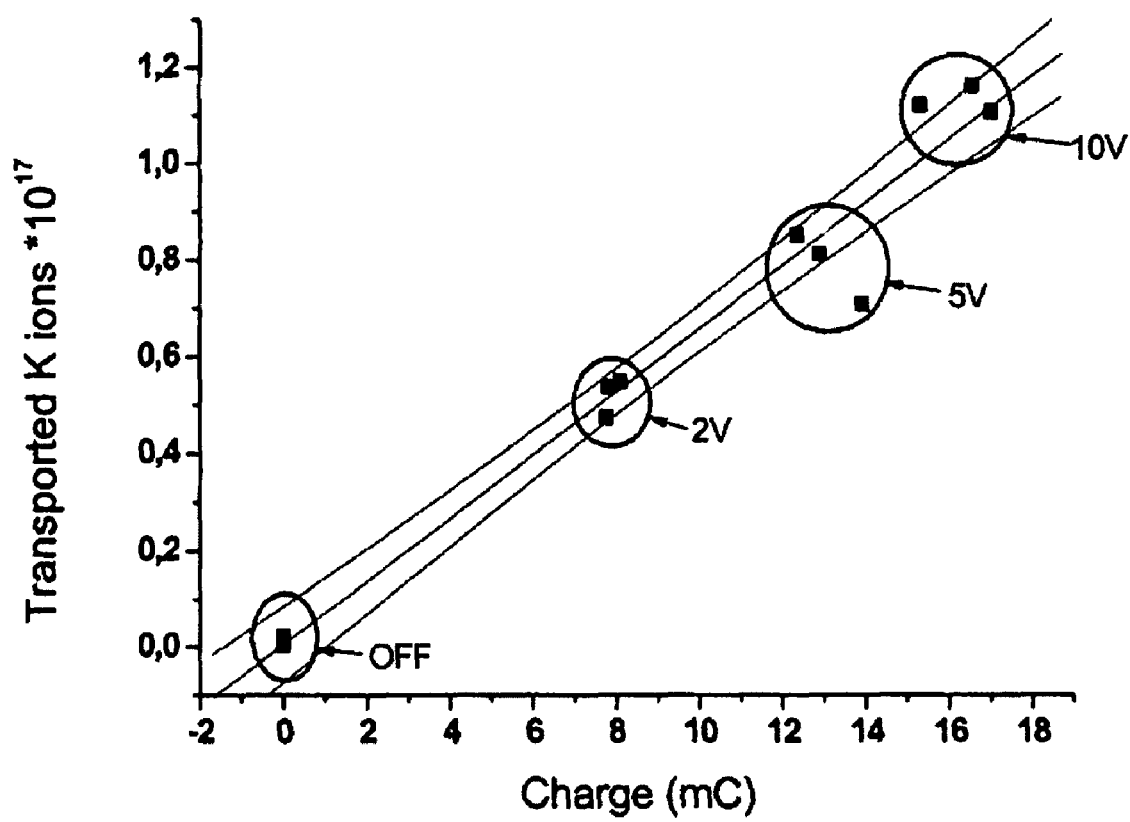
FIG. 11 shows transported $K^+$ ions for different voltages in Example 6.

A. Source electrolyte (2) was 0.1 M KCl. Voltages of 1 V were applied between source and source resetting electrode and between target and target resetting electrode, respectively. The ion transport device was operated for 10 min. by applying a voltage of 2 V, 5 V and 10 V, respectively between source and target electrodes. During operation, the current between source and target electrodes was registered. By integration of the current, the total charge transported between source and target electrodes was obtained. FIG. 11 shows high correlation between total charge transported and number of transported $K^+$ ions (OFF denotes the condition for diffusion of $K^+$ from source electrolyte to target electrolyte during 25 min).

B. The ion transport device was operated with different combinations of initial $K^+$ concentrations i the source and target electrolytes (Table 1 below). A voltage of 10 V was applied between source and target electrodes and voltages of 1 V were applied between source and source resetting electrode and between target and target resetting electrode, respectively.

TABLE 1

| Initial [$K^+$] in source electrolyte | Initial [$K^+$] in target electrolyte | Final [$K^+$] in target electrolyte |
|---|---|---|
| 1 M | 0 | 2.1 mM |
| 1 M | 2.4 mM | 4.3 mM |
| 2.8 mM | 0 | 1.1 mM |
| 2.8 mM | 2.4 mM | 3.3 mM |

Table 1 shows that it possible to transport ions from a source electrolyte of lower $K^+$ concentration to a target electrolyte of higher $K^+$ concentration. Table 1 also shows that a higher concentration in the source electrolyte provides for increased transport.

Example 7

Electronically Controlled pH Gradients and Proton Oscillations

The ion transport device may also be used for transport of protons in order to create pH gradients. An ion transport device manufactured essentially according to Preparatory example 3 was used to perform the following experiment.

The channel |C1–C2| and target |T1–T2| potentials were applied with a Keithley 2602 source meter and controlled through a Labview program, which also measured the current. The source potential |S1–S2| was applied with an external power supply and that current was not measured. The source (2) and target (4) electrolytes were deposited (150 µl) with micropipettes. The source electrolyte was HCl with pH=0 and the target electrolyte was KCl with pH=5 or $CaCl_2$ with pH=7. Spatially resolved proton transport was studied with ordinary pH paper (Merck) placed in the target electrolyte above the target electrode. The impermeable backside of the paper was peeled of before use. Judging from the colour change of the PEDOT:PSS underneath and the current levels when potentials were applied, the presence of the paper did not seem to interfere with the electrochemical switch of the target electrode. The part of the pH paper used for spatially resolved measurements was yellow at pH=5 and dark red at pH=2. Pictures of the paper were acquired with a Scalar USB camera. When the average pH of the entire target electrolyte was analyzed, 100 µl liquid was withdrawn and placed on a strip of pH paper.

Images of the pH paper were analyzed in a simple Matlab program. The levels of the green channel changed the most when the pH paper switched color and was therefore used to evaluate pH. Only the direction along the target electrode was analyzed, i.e. each value is the mean of all intensities along a column of pixels. The intensity of the green channel was very approximately calibrated to pH values with solutions of known pH. Reference points that did not change pH were used to correct the images from fluctuations in surrounding light and effects from the color change of the underlying PEDOT:PSS upon oxidation and reduction. The pH in the liquid was assumed to be uniform immediately (t=0) after deposition onto the device.

When the potentials are applied (source potential=target potential=1 V and channel potential=10 V), protons from the source electrolyte are delivered through the channel and released into the target electrolyte. During 10 min, the pH of KCl in the target electrolyte drops from 5 to 3 or if $CaCl_2$ is used in the target electrolyte, from 7 to about 3, i.e. a large part of the physiologically interesting pH range is covered. This alteration in pH is of course only a rough estimate of the exact number of transported protons but the concentration of free protons has increased with approximately 1 mM in both cases. That corresponds to 150 nmol of transported ions (electrolyte volume is 150 µl). The integrated channel current was ~15 mC, i.e. 155 nmol of electrons (15 mC divided by the charge of one electron and Avogadro's number), which means that the efficiency of the device is close to 100%. This is also what we see when e.g. $K^+$ is transported and the concentrations are measured more accurately, e.g. with atomic absorption spectroscopy. If no potentials are applied, no change in pH is detected. Thus, the on/off of the device is at least 1000 (probably higher locally) when pumping protons.

Figure 12:
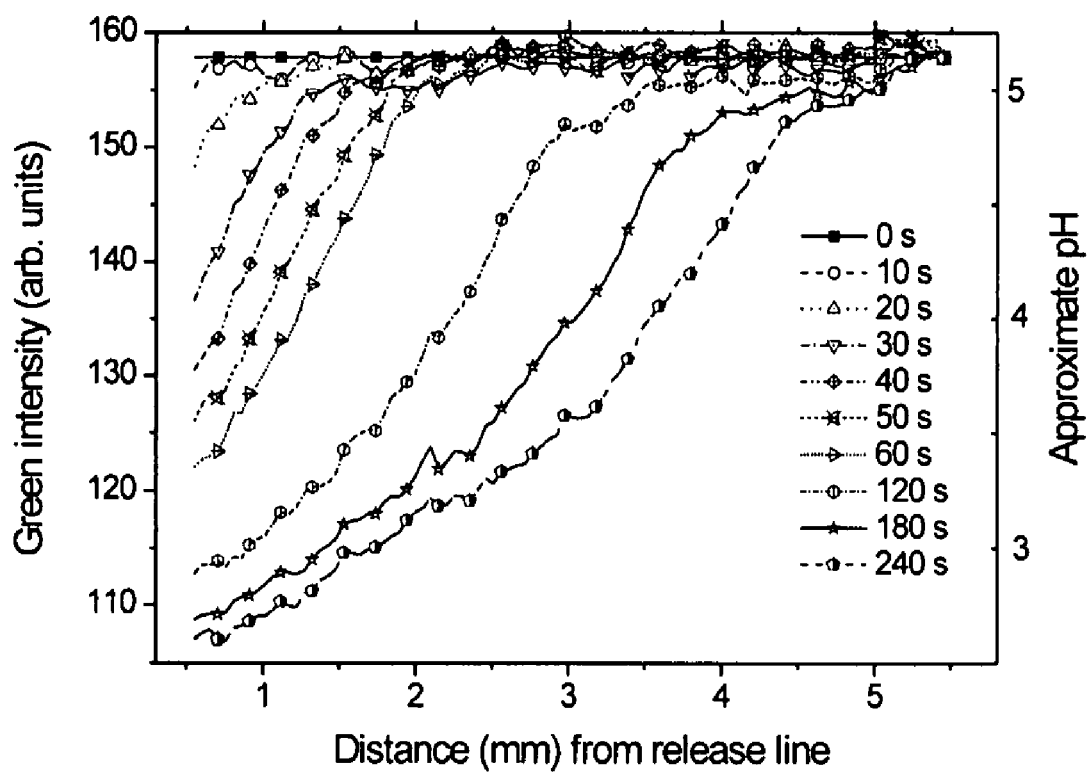
FIG. 12 shows the change in pH along the target electrode at constantly applied potentials in Example 7 (source potential=target potential=1 V and the channel potential=5 V).

Maybe more interesting than the pH of the entire electrolyte is to study what happens locally, close to the line where ions (protons) are released. FIG. 12 shows the pH distribution along the target electrode (each point is the average of all pixels in a column) at different times when the potentials (source potential=target potential=1 V and the channel potential=5 V) are constantly applied. It is evident from FIG. 12 that the delivery of new ions is faster than the diffusion process that balances the pH in the entire target electrolyte. The pH close to the line of release constantly decreases as more and more protons are transported. At the same time, the proton concentration is evened out by diffusion and the pH gradient stretches along 5 mm of the 7 mm wide target electrode, already after 4 min.

The faster the protons (or other ions) are supplied, the steeper the gradient, which means that it is possible to tune the shape of the gradient by balancing the transport rate (by adjusting voltages and times) with the diffusion rate in the receiving electrolyte.

Figure 13:
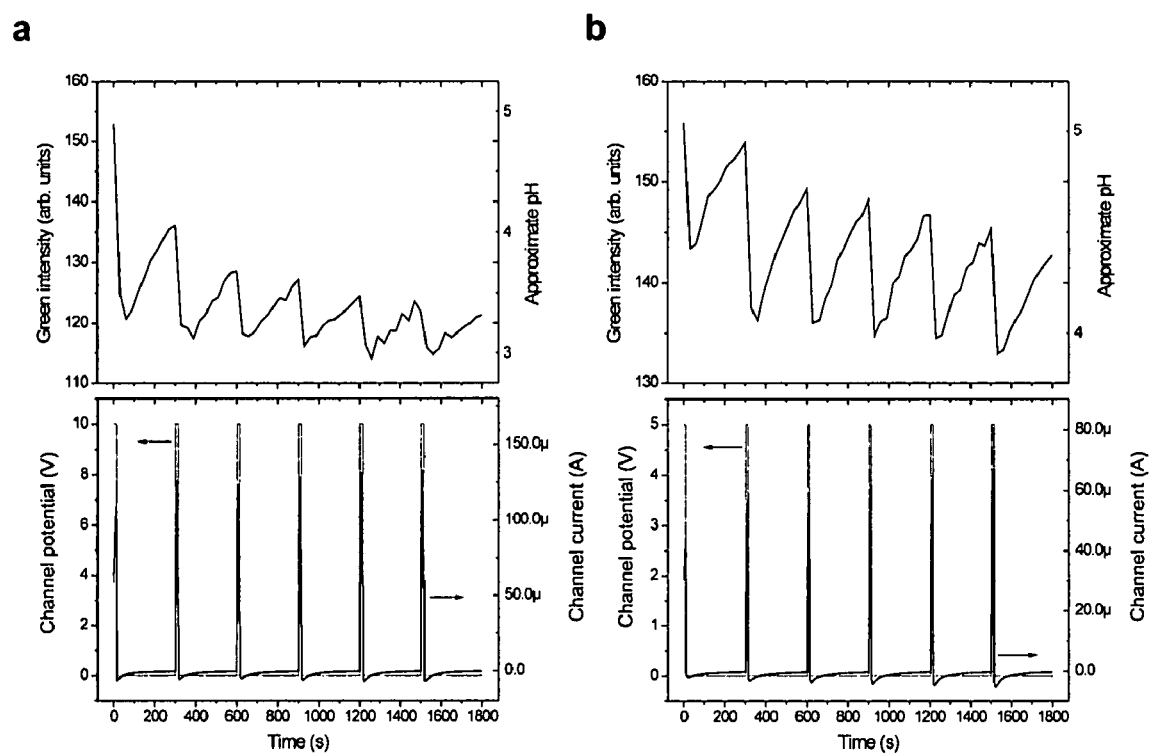
FIG. 13 shows oscillations in the target electrolyte close to the release line as disclosed in Example 7. Source potential=target potential=1 V during the pulses, otherwise 0 V. (a) 15 s pulses with channel potential=10 V. (b) 10 s pulses with channel potential=5 V.

Many biological signals are oscillatory with specific frequencies. Therefore, we tested to drive the ion pump with short pulsed signals to create local oscillations. The column of pixels closest (~0.5 mm into the electrolyte) to the release line was analyzed during each run and the results of 15 s pulses with channel potential=10 V and 10 s pulses with channel potential=5 V are presented in FIG. 13 *a* and *b*, respectively.

The experiments show that it is possible to create ion concentration oscillations by matching the pulses with ion diffusion in the electrolyte. The period time of the oscillations created here is about 5 min, which corresponds very well to the time scales observed e.g. with calcium responses in (and between) epithelial cells.

Example 8

Transport of Acetylcholine Using an Electrically Controlled Ion Transport Device As an example of transport of larger molecules, acetylcholine was transported using the ion transport device of the invention.

The ion transport device used in this example was manufactured essentially according to Preparatory example 3.

The channel |C1–C2| and target |T1–T2| potentials were applied with a Keithley 2602 source meter and controlled through a Labview program, which also measured the current. The source potential |S1–S2| was applied with an external power supply and that current was not measured. The source (2) and target (4) electrolytes were deposited (150 μl) with micropipettes. The source electrolyte was 0.1 M acetylcholine chloride and the target electrolyte was 0.1 M calcium acetate.

Figure 14:
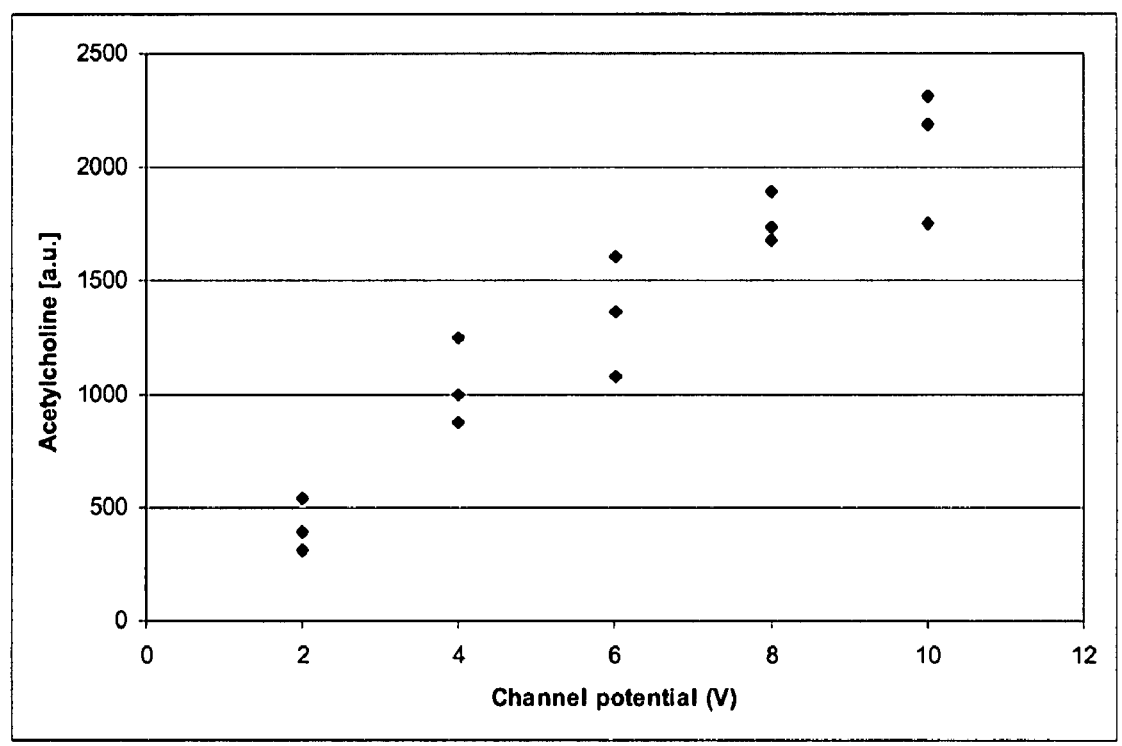
FIG. 14 shows transport of acetylcholine at constantly applied potentials in Example 8 (source potential=target potential=1 V, the channel potential was varied from 2 to 10 V).

When the potentials (source potential=target potential=1 V, the channel potential was varied from 2 to 10 V) were applied, acetylcholine from the source electrolyte was delivered through the channel and released into the target electrolyte. When no potentials were applied, no transport of acetylcholine was observed. The results after 1200 s of transport are presented in FIG. 14.

The invention claimed is:

1. A device for electrically controlled transport of ions between a source and a target electrolyte, comprising:
    a source electrode and a target electrode, each capable of conducting ions and electrons, wherein said source electrode is arranged to receive ions from said source electrolyte and said target electrode is arranged to release ions to said target electrolyte, and
    a material configured to retain one of said source and target electrolytes on the device, arranged such that the electrolyte is in contact with the desired electrodes, and
    an ion-conductive channel, arranged to receive ions from said source electrode, to release ions to said target electrode and to provide an ionic connection between said source and said target electrodes,
    wherein said electrodes and said ion-conductive channel are formed of solid or semi-solid materials which are directly or indirectly attached to a support, and
    further comprising a current-limiting material that limits an electronic current between said source and said target electrodes, such that at least after a voltage is applied across said channel a potential difference between said source and target electrodes is maintained, which effects ion transport from said source to said target electrode.

2. A device according to claim 1, further comprising another material configured to retain the other of said source and target electrolytes on the device, arranged such that the respective electrolyte is in contact with the desired electrodes.

3. A device according to claim 1, wherein said material configured to retain a source or target electrolyte comprises walls for retaining the electrolyte.

4. A device according to claim 1, wherein said material configured to retain a source or target electrolyte comprises openings in a partial encapsulation of the device.

5. A device according to claim 1, wherein said material configured to retain a source or target electrolyte is in the form of a container.

6. A device according to claim 1, wherein said material configured to retain a source or target electrolyte comprises a suitable chemical or physical treatment of the device surface.

7. A device according to claim 1, wherein said current-limiting material comprises a portion of said ion-conductive channel having a reduced electron conductivity compared to the electron conductivity of said source and target electrodes, respectively.

8. A device according to claim 1, wherein said electrodes each comprises electrochemically active material.

9. A device according to claim 8, wherein said current-limiting material comprises a first electrode, which first electrode is different from both said source electrode and said target electrode, and which is in electrostatic or ionic contact with a second electrode, which second electrode is one and the same as either said source electrode or said target electrode, and which electrodes are arranged such that after a voltage is applied between said source and target electrodes said electronic current between said source electrode and said target electrode is limited.

10. A device according to claim 1, wherein said ion-conducting channel comprises electrochemically active material.

11. A device according to claim 10, wherein said electrodes and said ion-conductive channel is formed of the same material and arranged as a unitary element.

12. A device according to claim 1, further comprising a source resetting electrode, arranged to be in electrostatic or ionic contact with said source electrolyte.

13. A device according to claim 12, further comprising a target resetting electrode, arranged to be in electrostatic or ionic contact with said target electrolyte.

14. A device according to claim 12, wherein said source resetting electrode comprises electrochemically active material.

15. A device according to claim 1, wherein said ion-conductive channel is a layer, which is directly or indirectly attached to said support.

16. A device according to claim 1, wherein said electrodes each is a layer, which is directly or indirectly attached to said support.

17. A device according to claim 1, wherein each of said source electrolyte and said target electrolyte is in direct physical contact with said ion-conductive channel.

18. A device according to claim 1, wherein said source electrode is arranged between said support and said source electrolyte.

19. A device according to claim 1, wherein said ion-conducting channel overlaps a portion of said source and target electrodes.

20. A device according to claim 1, wherein said ion-conducting channel is arranged in direct physical contact with said source and said target electrode.

21. A device according to claim 1, wherein said source electrode is arranged in direct physical contact with said source electrolyte and said target electrolyte is in physical contact with said target electrolyte.

22. A device according to claim 1, wherein said source electrode is in physical contact with a first electrical conducting wire and said target electrode each is in direct physical contact with a second electrical conducting wire.

23. A device according to claim 1, wherein said support is flexible.

24. A device according to claim 1, wherein said support is a sheet.

25. Device according to claim 1, wherein said source or target electrode comprise an organic material.

26. Device according to claim 25, wherein said organic material comprises an electrically conductive polymer.

27. Device according to claim 26, wherein said electrically conductive polymer is selected from the group consisting of polythiophenes, polypyrroles, polyanilines, polyisothianaphthalenes, polyphenylene vinylenes and copolymers thereof.

28. Device according to claim 27, wherein said polymer is poly(3,4-ethylenedioxythiophene).

29. Device according to claim 25, wherein said organic material further comprises a polyelectrolyte compound.

30. Device according to claim 29, wherein said polyelectrolyte compound is poly(styrene sulfonic acid) or a salt thereof.

31. Device according to claim 1, wherein said electrodes further comprise a hydrogel.

32. Device according to claim 31, wherein said hydrogel is based on a polymer selected from the group consisting of poly(2-hydroxyethyl methacrylate), poly(acrylamide), poly(acrylic acid), poly(styrene sulfonic acid), agarose, dextran, polyvinyl alcohol, polyvinyl pyrrolidone, polyethylene glycol and chitosan.

33. Device according to claim 1, wherein at least one of the electrodes comprises biocompatible material.

34. Device according to claim 1, wherein the ion-conductive channel comprises an organic material.

35. Device according to claim 34, wherein said organic material comprises a polymer.

36. Device according to claim 35, wherein said polymer is an electrically conducting polymer.

37. Device according to claim 36, wherein a portion of said polymer is in an overoxidized state.

38. Device according to claim 36, wherein said electrically conductive polymer is selected from the group consisting of polythiophenes, polypyrroles, polyanilines, polyisothianaphthalenes, polyphenylene vinylenes and copolymers thereof.

39. Device according to claim 38, wherein said organic material comprises overoxidized poly(3,4-ethylenedioxythiophene):poly(styrene sulfonic acid).

40. Device according to claim 34, wherein said organic material is a hydrogel.

41. Device according to claim 40, wherein said hydrogel is based on a polymer selected from the group consisting of poly(2-hydroxyethyl methacrylate), poly(acrylamide), poly(acrylic acid), poly(styrene sulfonic acid), agarose, dextran, polyvinyl alcohol, polyvinyl pyrrolidone, polyethylene glycol and chitosan.

42. Device according to claim 34, wherein said organic material is a polyelectrolyte.

43. Device according to claim 42, wherein said polyelectrolyte is selected from the group consisting of poly(styrene sulfonic acid) and poly(acrylic acid).

44. A device according to claim 1, comprising a further target electrode arranged to release ions to a further target electrolyte and a further ion-conductive channel, arranged to receive ions from said source electrode and to release ions to said further target electrode.

45. A device according to claim 1, comprising a further source electrode arranged to receive ions from a further source electrolyte and a further ion-conductive channel, arranged to receive ions from said further source electrode and to release ions to said target electrode.

46. An apparatus for transporting ions to or from, respectively, a cell, comprising a device as defined in claim 1 and a related cell contact site arranged to provide ionic contact between the cell and the target or source electrolyte, respectively.

47. An apparatus according to claim 46, comprising a multiplicity of said devices and their related cell contact sites, the devices and their related cell contact sites preferably being arranged to create a matrix system thereof, wherein each device may be addressed individually for ion transport purposes.

48. An apparatus according to claim 46, wherein each device and its related cell contact site is arranged to provide ionic contact between a single cell and the target or source electrolyte, respectively.

49. An apparatus according to claim 46, wherein said ionic contact between the cell and the target or source electrolyte is provided through a disruption in an insulating layer arranged between the cell and the device.

* * * * *